(12) United States Patent
Rance et al.

(10) Patent No.: US 6,963,021 B2
(45) Date of Patent: Nov. 8, 2005

(54) CHIMERIC EXPRESSION PROMOTERS ORIGINATING FROM COMMELINA YELLOW MOTTLE VIRUS AND CASSAVA VEIN MOSAIC VIRUS

(75) Inventors: Iann Rance, Aobiat (FR); Veronique Gruber, Romagnat (FR); Manfred Theisen, Chamalieres (FR)

(73) Assignee: Meristem Therapeutics, St. Etienne (FR)

( * ) Notice: Subject to any disclaimer, the term of this patent is extended or adjusted under 35 U.S.C. 154(b) by 68 days.

(21) Appl. No.: 09/963,803

(22) Filed: Sep. 26, 2001

(65) Prior Publication Data

US 2003/0028922 A1 Feb. 6, 2003

Related U.S. Application Data

(63) Continuation of application No. PCT/IB00/00370, filed on Mar. 29, 2000.

(30) Foreign Application Priority Data

Mar. 29, 1999 (FR) .............................. 99 03925

(51) Int. Cl.⁷ .................. C12N 15/82; C12N 15/11; C12N 15/63; C12N 5/10; C07H 21/04
(52) U.S. Cl. ..................... 800/278; 800/298; 536/23.1; 536/24.1; 435/320.1; 435/419
(58) Field of Search ................................ 536/23.1, 24.1; 435/320.1, 419; 800/278, 298

(56) References Cited

FOREIGN PATENT DOCUMENTS

| WO | WO97/48819 | 6/1997 | ........... C12P/21/06 |
|---|---|---|---|
| WO | WO 97/48819 | * 12/1997 | |

OTHER PUBLICATIONS

Lewin, Genes III, (1987) John Wiley & Sons, Inc.*

* cited by examiner

*Primary Examiner*—David Guzo
*Assistant Examiner*—Daniel M. Sullivan
(74) *Attorney, Agent, or Firm*—Kathleen M. Williams; Palmer & Dodge LLP

(57) ABSTRACT

The present invention relates to a chimeric expression promoter comprising at least one nucleic acid sequence derived from a first plant promoter containing a plant vascular expression promoter region, where the plant vascular expression promoter region is replaced with a nucleic acid sequence derived from a second plant promoter and containing a plant green tissue expression promoter region. The present invention also relates to a vector, a cell, and a transgenic plant containing the chimeric expression promoter, as well as a method of nucleic acid expresssion using the chimeric expression promoter.

38 Claims, 7 Drawing Sheets pMRT1144 pMRT1092 pCaMV35S luc pMRT1082 pMRT1116 pMRT1117 pMRT1146 pMRT1147

SEQUENCE LISTING

```
<160> NUMBER OF SEQ ID NOS: 39

<210> SEQ ID NO 1
<211> LENGTH: 243
<212> TYPE: DNA
<213> ORGANISM: Artificial Sequence
<220> FEATURE:
<223> OTHER INFORMATION: 243 bp Fragment from the intergenic region of
      commelina yellow mottle virus
<220> FEATURE:
<221> NAME/KEY: promoter
<222> LOCATION: (1)..(243)
<223> OTHER INFORMATION:

<400> SEQUENCE: 1
atccgccgtc atcaatgaca tcatcacagt actgaggaga tgaatactta gccatgaagt      60
agcgtgcgaa tattacctat gcctttattc gcagcgttag tggcactgaa aggcataaag     120
tttgttcgtt cttatcaaaa acgaatctta tctttgtaac ttggttaccc ggtatgccgg     180
ttcccaagct ttatttcctt atttaagcac ttgtgtagta gcttagaaaa ccaacacaac     240
aac                                                                   243

<210> SEQ ID NO 2
<211> LENGTH: 515
<212> TYPE: DNA
<213> ORGANISM: Artificial Sequence
<220> FEATURE:
<223> OTHER INFORMATION: Promoter from the intergenic region of Cassava
      Vein Mosaic virus of 515 bp in length EMBL
<220> FEATURE:
<221> NAME/KEY: promoter
<222> LOCATION: (1)..(515)
<223> OTHER INFORMATION:
```

-continued

<400> SEQUENCE: 2

```
ccagaaggta attatccaag atgtagcatc aagaatccaa tgtttacggg aaaaactatg      60
gaagtattat gtgagctcag caagaagcag atcaatatgc ggcacatatg caacctatgt     120
tcaaaaatga agaatgtaca gatacaagat cctatactgc agaatacga agaagaatac     180
gtagaaattg aaaagaaga accaggcgaa gaaaagaatc ttgaagacgt aagcactgac     240
gacaacaatg aaaagaagaa gataaggtcg gtgattgtga agagacata gaggacacat     300
gtaaggtgga aatgtaagg gcggaaagta accttatcac aaaggaatct tatcccccac     360
tacttatcct tttatatttt tccgtgtcat ttttgccctt gagttttcct atataaggaa     420
ccaagttcgg catttgtgaa acaagaaaaa aatttggtgt aagctatttt ctttgaagta     480
ctgaggatac aacttcagag aaatttgtaa gtttg                                515
```

<210> SEQ ID NO 3
<211> LENGTH: 317
<212> TYPE: DNA
<213> ORGANISM: Artificial Sequence
<220> FEATURE:
<223> OTHER INFORMATION: Promoter MPr1116
<220> FEATURE:
<221> NAME/KEY: promoter
<222> LOCATION: (1)..(317)
<223> OTHER INFORMATION:

<400> SEQUENCE: 3

```
aagcttgcat gctgcagact agtatccgcc gtcatcaatg acatcatcac agtactgagg      60
agatgaatag ctagccatga cactctgtgc gaatattgaa gacgtaagca ctgacgacaa     120
caatgaaaag aagaagataa ggtcggtgat tgtgaaagag acatagagga cacatgtaag     180
gtggaaaatg taagggcgga agtaaccctt atgcatttgt aacttggtta cccggtatgc     240
cggttcccaa gctttattc cttatttaag cacttgtgta gtagcttaga aaaccaacac     300
aacaacctag aggatcc                                                    317
```

<210> SEQ ID NO 4
<211> LENGTH: 348
<212> TYPE: DNA
<213> ORGANISM: Artificial Sequence
<220> FEATURE:
<223> OTHER INFORMATION: promoter MPr1117
<220> FEATURE:
<221> NAME/KEY: promoter
<222> LOCATION: (1)..(348)
<223> OTHER INFORMATION:

<400> SEQUENCE: 4

```
aagcttgcat gcctgcagac tagtatccgc cgtcatcaat gacatcatca gactagtatc      60
cgccgtcatc aatgacatca tcacagtact gaggagatga atagctagcc atgacactct     120
gtgcgaatat tgaagacgta agcactgacg acaacaatga aagaagaag ataaggtcgg     180
tgattgtgaa gagacataga ggacacatgt aaggtggaaa atgtaagggc ggaaagtaac     240
cttatgcatt tgtaacttgg ttacccggta tgctggttcc caagctttat ttccttattt     300
aaacttgtgt agtagcttag aaaaccaaca caacaaccta gaggatcc                  348
```

<210> SEQ ID NO 5
<211> LENGTH: 371
<212> TYPE: DNA
<213> ORGANISM: Artificial Sequence
<220> FEATURE:

<223> OTHER INFORMATION: promoter MPr1146
<220> FEATURE:
<221> NAME/KEY: promoter
<222> LOCATION: (1)..(371)
<223> OTHER INFORMATION:

<400> SEQUENCE: 5

```
aagcttgcat gctgcagact agtatccgcc gtcatcaatg acatcatcac agtactgagg      60
agatgaatag ctagtgattg atgtgatatc aagattgatg tgatatctcc actgacgtaa     120
gggatgacgc atgccactct gtgcgaatat tgaagacgta agcactgacg acaacaatga     180
aaagaagaag ataaggtcgg tgattgtgaa agagacatag aggacacatg taaggtggaa     240
aatgtaaggg cggaaagtaa ccttatgcat ttgtaacttg gttacccggt atgccggttc     300
ccaagcttta tttccttatt taagcacttg tgtagtagct tagaaaacca acacaacaac     360
ctagaggatc c                                                           371
```

<210> SEQ ID NO 6
<211> LENGTH: 398
<212> TYPE: DNA
<213> ORGANISM: Artificial Sequence
<220> FEATURE:
<223> OTHER INFORMATION: promoter MPr1147
<220> FEATURE:
<221> NAME/KEY: promoter
<222> LOCATION: (1)..(398)
<223> OTHER INFORMATION:

<400> SEQUENCE: 6

```
aagcttgcat gcctgcagac tagtatccgc cgtcatcaat gacatcatca gactagtatc      60
cgccgtcatc aatgacatca tcacagtact gaggagatga atagctagcc tgcagactag     120
tggattgatg tgatatctcc actgacgtaa gggatgacgc atgccactct gtgcgaatat     180
tgaagacgta agcactgacg acaacaatga aaagaagaag ataaggtcgg tgattgtgaa     240
gagacataga ggacacatgt aaggtggaaa atgtaagggc ggaaagtaac cttatgcatt     300
tgtaacttgg ttacccggta tgctggttcc caagctttat ttccttattt aaacttgtgt     360
agtagcttag aaaaccaaca caacaaccta gaggatcc                             398
```

<210> SEQ ID NO 7
<211> LENGTH: 301
<212> TYPE: DNA
<213> ORGANISM: Artificial Sequence
<220> FEATURE:
<223> OTHER INFORMATION: promoter MPr1154
<220> FEATURE:
<221> NAME/KEY: promoter
<222> LOCATION: (1)..(301)
<223> OTHER INFORMATION:

<400> SEQUENCE: 7

```
aagcttgcat gcctgcagac tagtggattg atgtgatatc tccactgacg taagggatga      60
cgcatgccac tctgtgcgaa tattgaagac gtaagcactg acgacaacaa tgaaaagaag     120
aagataaggt cggtgattgt gaagagacat agaggacaca tgtaaggtgg aaaatgtaag     180
ggcggaaagt aaccttatgc atttgtaact tggttacccg gtatgctggt tcccaagctt     240
tatttcctta tttaaacttg tgtagtagct tagaaaacca acacaacaac ctagaggatc     300
c                                                                      301
```

<210> SEQ ID NO 8

<210> SEQ ID NO 8
<211> LENGTH: 65
<212> TYPE: DNA
<213> ORGANISM: Artificial Sequence
<220> FEATURE:
<223> OTHER INFORMATION: Directional desoxynucleotide building block
      S1

<400> SEQUENCE: 8
catgctgcag actagtatcc gccgtcatca atgacatcat cacagtactg aggagatgaa    60
tagct                                                                65

<210> SEQ ID NO 9
<211> LENGTH: 60
<212> TYPE: DNA
<213> ORGANISM: Artificial Sequence
<220> FEATURE:
<223> OTHER INFORMATION: Directional desoxynucleotide building block
      S2

<400> SEQUENCE: 9
agccatgaca ctctgtgcga atattgaaga cgtaagcact gacgacaaca atgaaaagaa    60

<210> SEQ ID NO 10
<211> LENGTH: 62
<212> TYPE: DNA
<213> ORGANISM: Artificial Sequence
<220> FEATURE:
<223> OTHER INFORMATION: Directional desoxynucleotide building block
      S3

<400> SEQUENCE: 10
gaagataagg tcggtgattg tgaaagagac atagaggaca catgtaaggt ggaaaatgta    60
ag                                                                   62

<210> SEQ ID NO 11
<211> LENGTH: 63
<212> TYPE: DNA
<213> ORGANISM: Artificial Sequence
<220> FEATURE:
<223> OTHER INFORMATION: Directional desoxynucleotide building block
      S4

<400> SEQUENCE: 11
ggcggaaagt aaccttatgc atttgtaact tggttacccg gtatgccggt tcccaagctt    60
tat                                                                  63

<210> SEQ ID NO 12
<211> LENGTH: 63
<212> TYPE: DNA
<213> ORGANISM: Artificial Sequence
<220> FEATURE:
<223> OTHER INFORMATION: Directional desoxynucleotide building block
      S5

<400> SEQUENCE: 12
ttccttattt aagcacttgt gtagtagctt agaaaaccaa cacaacaacc tagaggatcc    60
ccg                                                                  63

<210> SEQ ID NO 13
<211> LENGTH: 63
<212> TYPE: DNA
<213> ORGANISM: Artificial Sequence
<220> FEATURE:
<223> OTHER INFORMATION: Directional desoxynucleotide building block
      S6

<400> SEQUENCE: 13
catgctgcag actagtggat tgatgtgata tctccactga cgtaagggat gacgcatgcc    60
act                                                                 63

<210> SEQ ID NO 14
<211> LENGTH: 79
<212> TYPE: DNA
<213> ORGANISM: Artificial Sequence
<220> FEATURE:
<223> OTHER INFORMATION: Directional desoxynucleotide building block
     S7

<400> SEQUENCE: 14
catgctgcag actagtgatt gatgtgatat caagattgat gtgatatctc cactgacgta    60
agggatgacg catgccact                                                79

<210> SEQ ID NO 15
<211> LENGTH: 34
<212> TYPE: DNA
<213> ORGANISM: Artificial Sequence
<220> FEATURE:
<223> OTHER INFORMATION: Guide desoxynucleotide building
     block G1

<400> SEQUENCE: 15
gactcctcta cttatcgatc ggtactgtga gaca                               34

<210> SEQ ID NO 16
<211> LENGTH: 33
<212> TYPE: DNA
<213> ORGANISM: Artificial Sequence
<220> FEATURE:
<223> OTHER INFORMATION: Guide desoxynucleotide building
     block G2

<400> SEQUENCE: 16
gctgttgtta cttttcttct tctattccag cca                                33

<210> SEQ ID NO 17
<211> LENGTH: 31
<212> TYPE: DNA
<213> ORGANISM: Artificial Sequence
<220> FEATURE:
<223> OTHER INFORMATION: Guide desoxynucleotide building
     block G3

<400> SEQUENCE: 17
attccacctt ttacattccc gcctttcatt g                                  31

<210> SEQ ID NO 18
<211> LENGTH: 32
<212> TYPE: DNA
<213> ORGANISM: Artificial Sequence
<220> FEATURE:
<223> OTHER INFORMATION: Guide desoxynucleotide building
     block G4

<400> SEQUENCE: 18
caagggttcg aaataaagga ataaattcgt ga                                 32

<210> SEQ ID NO 19
<211> LENGTH: 393
<212> TYPE: DNA
<213> ORGANISM: Artificial Sequence

```
<220> FEATURE:
<223> OTHER INFORMATION: promoter MPr1162
<220> FEATURE:
<221> NAME/KEY: promoter
<222> LOCATION: (1)..(393)
<223> OTHER INFORMATION:

<400> SEQUENCE: 19
aagcttgcat gcctgcagca ctagtatccg ccgtcatcaa tgacatcatc acagtactga      60
ggagatgaat agctagccat gacactctgt gcgaatattg aagacgtaag cactgacgac     120
aacaatgaaa agaagaagat aaggtcggtg attgtgaaag agacatagag gacacatgta     180
aggtggaaaa tgtaagggcg gaaagtaacc ttatgcattt gtaatttggt tacgactagt     240
gattgatgtg atatcaagat tgatgtgata tctccactga cgtaagggat gacgcatgcc     300
acgttacccg gtatgccggt tcccaagctt tatttcctta tttaagcact tgtgtagtag     360
cttagaaaac caacacaaca acctagagga tcc                                  393

<210> SEQ ID NO 20
<211> LENGTH: 462
<212> TYPE: DNA
<213> ORGANISM: Artificial Sequence
<220> FEATURE:
<223> OTHER INFORMATION: promoter MPr1163
<220> FEATURE:
<221> NAME/KEY: promoter
<222> LOCATION: (1)..(462)
<223> OTHER INFORMATION:

<400> SEQUENCE: 20
aagcttgcat gcctgcagca ctagtatccg ccgtcatcaa tgacatcatc acagtactga      60
ggagatgaat agctagccat gacactctgt gcgaatattg aagacgtaag cactgacgac     120
aacaatgaaa agaagaagat aaggtcggtg attgtgaaag agacatagag gacacatgta     180
aggtggaaaa tgtaagggcg gaaagtaacc ttatgcattt gtaatttggt tacgactagt     240
gattgatgtg atatcaagat tgatgtgata tctccactga cgtaagggat gacgcatgcc     300
acgactagtg attgatgtga tatcaagatt gatgtgatat ctccactgac gtaagggatg     360
acgcatgcca cgttacccgg tatgccggtt cccaagcttt atttccttat ttaagcactt     420
gtgtagtagc ttagaaaacc aacacaacaa cctagaggat cc                        462

<210> SEQ ID NO 21
<211> LENGTH: 392
<212> TYPE: DNA
<213> ORGANISM: Artificial Sequence
<220> FEATURE:
<223> OTHER INFORMATION: promoter MPr1164
<220> FEATURE:
<221> NAME/KEY: promoter
<222> LOCATION: (1)..(392)
<223> OTHER INFORMATION:

<400> SEQUENCE: 21
aagcttgcat gcctgcagca ctagtatccg ccgtcatcaa tgacatcatc acagtactga      60
ggagatgaat agctagccat gacactctgt gcgaatattg aagacgtaag cactgacgac     120
aacaatgaaa agaagaagat aaggtcggtg attgtgaaag agacatagag gacacatgta     180
aggtggaaaa tgtaagggcg gaaagtaacc ttatgcattt gtaatttggt tacgtggcat     240
gcgtcatccc ttacgtcagt ggagatatca catcaatctt gatatcacat caatcactag     300
tcgttacccg gtatgccggt tcccaagctt tatttcctta tttaagcact tgtgtagtag     360
```

```
cttagaaaac caacacaaca actagaggat cc                                  392
```

```
<210> SEQ ID NO 22
<211> LENGTH: 600
<212> TYPE: DNA
<213> ORGANISM: Artificial Sequence
<220> FEATURE:
<223> OTHER INFORMATION: promoter MPr1165
<220> FEATURE:
<221> NAME/KEY: promoter
<222> LOCATION: (1)..(600)
<223> OTHER INFORMATION:

<400> SEQUENCE: 22
aagcttgcat gcctgcagca ctagtatccg ccgtcatcaa tgacatcatc acagtactga    60
ggagatgaat agctagccat gacactctgt gcgaatattg aagacgtaag cactgacgac   120
aacaatgaaa agaagaagat aaggtcggtg attgtgaaag agacatagag gacacatgta   180
aggtggaaaa tgtaagggcg gaaagtaacc ttatgcattt gtaatttggt tacgactagt   240
gattgatgtg atatcaagat tgatgtgata tctccactga cgtaagggat gacgcatgcc   300
acgactagtg attgatgtga tatcaagatt gatgtgatat ctccactgac gtaagggatg   360
acgcatgcca cgactagtga ttgatgtgat atcaagattg atgtgatatc tccactgacg   420
taagggatga cgcatgccac gactagtgat tgatgtgata tcaagattga tgtgatatct   480
ccactgacgt aagggatgac gcatgccacg ttacccggta tgccggttcc caagctttat   540
ttccttattt aagcacttgt gtagtagctt agaaaaccaa cacaacaacc tagaggatcc   600
```

```
<210> SEQ ID NO 23
<211> LENGTH: 604
<212> TYPE: DNA
<213> ORGANISM: Artificial Sequence
<220> FEATURE:
<223> OTHER INFORMATION: promoter MPr1167
<220> FEATURE:
<221> NAME/KEY: promoter
<222> LOCATION: (1)..(604)
<223> OTHER INFORMATION:

<400> SEQUENCE: 23
aagcttgcat gcctgcagac tagtatccgc cgtcatcaat gacatcatca gactagtatc    60
cgccgtcatc aatgacatca tcacagtact gaggagatga atagctagtc tgcagactag   120
tggattgatg tgatatctcc actgacgtaa gggatgacgc atgccactct gtgcgaatat   180
tgaagacgta agcactgacg acaacaatga aaagaagaag ataaggtcgg tgattgtgaa   240
gagacataga ggacacatgt aaggtggaaa atgtaagggc ggaaagtaac cttatgcatt   300
tgtaacttgg ttacctagtg attgatgtga tatcaagatt gatgtgatat ctccactgac   360
gtaagggatg acgcatgcca cctagtgatt gatgtgatat caagattgat gtgatatctc   420
cactgacgta agggatgacg catgccacct agtgattgat gtgatatcaa gattgatgtg   480
atatctccac tgacgtaagg gatgacgcat gccacgttac ccggtatgct ggttcccaag   540
ctttatttcc ttatttaaac ttgtgtagta gcttagaaaa ccaacacaac aacctagagg   600
atcc                                                                 604
```

```
<210> SEQ ID NO 24
<211> LENGTH: 541
<212> TYPE: DNA
<213> ORGANISM: Artificial Sequence
<220> FEATURE:
<223> OTHER INFORMATION: promoter MPr1168
```

```
<220> FEATURE:
<221> NAME/KEY: promoter
<222> LOCATION: (1)..(541)
<223> OTHER INFORMATION:

<400> SEQUENCE: 24
aagcttgcat gcctgcagac tagtatccgc cgtcatcaat gacatcatca gactagtatc      60
cgccgtcatc aatgacatca tcacagtact gaggagatga atagctagtc tgcagactag     120
tggattgatg tgatatctcc actgacgtaa gggatgacgc atgccactct gtgcgaatat     180
tgaagacgta agcactgacg acaacaatga aaagaagaag ataaggtcgg tgattgtgaa     240
gagacataga ggacacatgt aaggtggaaa atgtaagggc ggaaagtaac cttatgcatt     300
tgtaacttgg ttacgactag tgattgatgt gatatcaaga ttgatgtgat atctccactg     360
acgtaaggga tgacgcatgc cacgactagt gattgatgtg atatcaagat tgatgtgata     420
tctccactga cgtaagggat gacgcatgcc acgttacccg gtatgctggt tcccaagctt     480
tatttcctta tttaaacttg tgtagtagct tagaaaacca acacaacaac ctagaggatc     540
c                                                                     541

<210> SEQ ID NO 25
<211> LENGTH: 472
<212> TYPE: DNA
<213> ORGANISM: Artificial Sequence
<220> FEATURE:
<223> OTHER INFORMATION: promoter MPr1169
<220> FEATURE:
<221> NAME/KEY: promoter
<222> LOCATION: (1)..(472)
<223> OTHER INFORMATION:

<400> SEQUENCE: 25
aagcttgcat gcctgcagac tagtatccgc cgtcatcaat gacatcatca gactagtatc      60
cgccgtcatc aatgacatca tcacagtact gaggagatga atagctagtc tgcagactag     120
tggattgatg tgatatctcc actgacgtaa gggatgacgc atgccactct gtgcgaatat     180
tgaagacgta agcactgacg acaacaatga aaagaagaag ataaggtcgg tgattgtgaa     240
gagacataga ggacacatgt aaggtggaaa atgtaagggc ggaaagtaac cttatgcatt     300
tgtaacttgg ttacgactag tgattgatgt gatatcaaga ttgatgtgat atctccactg     360
acgtaaggga tgacgcatgc cacgttaccc ggtatgctgg ttcccaagct ttatttcctt     420
atttaaactt gtgtagtagc ttagaaaacc aacacaacaa cctagaggat cc             472

<210> SEQ ID NO 26
<211> LENGTH: 20
<212> TYPE: DNA
<213> ORGANISM: Artificial Sequence
<220> FEATURE:
<223> OTHER INFORMATION: oligonucleotide probe

<400> SEQUENCE: 26
catgctgcag actagtatcc                                                  20

<210> SEQ ID NO 27
<211> LENGTH: 19
<212> TYPE: DNA
<213> ORGANISM: Artificial Sequence
<220> FEATURE:
<223> OTHER INFORMATION: oligonucleotide probe

<400> SEQUENCE: 27
```

-continued cggggatcct ctaggttgt                                      19

<210> SEQ ID NO 28
<211> LENGTH: 18
<212> TYPE: DNA
<213> ORGANISM: Artificial Sequence
<220> FEATURE:
<223> OTHER INFORMATION: deoxynucleotide primer

<400> SEQUENCE: 28
ttgatttcac gggttggg                                       18

<210> SEQ ID NO 29
<211> LENGTH: 21
<212> TYPE: DNA
<213> ORGANISM: Artificial Sequence
<220> FEATURE:
<223> OTHER INFORMATION: oligodeoxynucleotide primer

<400> SEQUENCE: 29
catgctgcag actagtggat t                                   21

<210> SEQ ID NO 30
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 30
cggggatcct ctaggtttct                                     20

<210> SEQ ID NO 31
<211> LENGTH: 18
<212> TYPE: DNA
<213> ORGANISM: Artificial Sequence
<220> FEATURE:
<223> OTHER INFORMATION: Deoxynucleotide primer

<400> SEQUENCE: 31
atttaggtga cactatag                                       18

<210> SEQ ID NO 32
<211> LENGTH: 23
<212> TYPE: DNA
<213> ORGANISM: Artificial Sequence
<220> FEATURE:
<223> OTHER INFORMATION: oligonucleotide primer

<400> SEQUENCE: 32
taaatccact gtgatatctt atg                                 23

<210> SEQ ID NO 33
<211> LENGTH: 29
<212> TYPE: DNA
<213> ORGANISM: Artificial Sequence
<220> FEATURE:
<223> OTHER INFORMATION: deoxynucleotide primer

<400> SEQUENCE: 33
atatgagact ctaattggat accgagggg                           29

<210> SEQ ID NO 34
<211> LENGTH: 70
<212> TYPE: DNA
<213> ORGANISM: Artificial Sequence

```
<220> FEATURE:
<223> OTHER INFORMATION: Directional Desoxynucleotide

<400> SEQUENCE: 34
ttcccttcaa acacatacaa attcagtaga gaagaaactc attactcttg agaaacctag     60
aggatccccg                                                           70

<210> SEQ ID NO 35
<211> LENGTH: 70
<212> TYPE: DNA
<213> ORGANISM: Artificial Sequence
<220> FEATURE:
<223> OTHER INFORMATION: Directional Desoxynucleotide

<400> SEQUENCE: 35
cacaaaaacc caatccacat ctttatcatc cattctataa aaaatcacct tctgtgtgtc     60
tctctttcga                                                           70

<210> SEQ ID NO 36
<211> LENGTH: 72
<212> TYPE: DNA
<213> ORGANISM: Artificial Sequence
<220> FEATURE:
<223> OTHER INFORMATION: Directional Desoxynucleotide

<400> SEQUENCE: 36
ctgtggcaca tctacattat ctaaatctaa gccacgtcgg aggataacat attcttccac     60
acatcttagc ca                                                        72

<210> SEQ ID NO 37
<211> LENGTH: 31
<212> TYPE: DNA
<213> ORGANISM: Artificial Sequence
<220> FEATURE:
<223> OTHER INFORMATION: directional oligodesoxynucleotides

<400> SEQUENCE: 37
tgtgtttgaa gggaatcgaa agagagacac a                                   31

<210> SEQ ID NO 38
<211> LENGTH: 30
<212> TYPE: DNA
<213> ORGANISM: Artificial Sequence
<220> FEATURE:
<223> OTHER INFORMATION: directional oligodesoxynucleotides

<400> SEQUENCE: 38
gattgggttt ttgtgtggct aagatgtgtg                                     30

<210> SEQ ID NO 39
<211> LENGTH: 28
<212> TYPE: DNA
<213> ORGANISM: Artificial Sequence
<220> FEATURE:
<223> OTHER INFORMATION: directional oligodesoxynucleotides

<400> SEQUENCE: 39
tgtagatgtg ccacagagtg gcatgcgt                                       28
```

CHIMERIC EXPRESSION PROMOTERS ORIGINATING FROM COMMELINA YELLOW MOTTLE VIRUS AND CASSAVA VEIN MOSAIC VIRUS

This application is a Continuation of PCT/IB00/00370, filed Mar. 29, 2000, which claims priority to FR 99/03925, filed Mar. 29, 1999. The entire teachings of the above applications are incorporated herein by reference.

The present invention relates to chimeric expression promoters, intended in particular for use in the field of plant biotechnology.

Expression promoters are in general known in the field of biotechnology and genetic manipulation. Insofar as plant biotechnology is more particularly concerned, the rate of expression of a gene coding for a polypeptide that it is desired to produce in a host cell is often dependent on the promoter used. The problem with this is that the various promoters commonly used are often limited to specific applications or tissues, simply because of their tissue specificity or expression strength. It is possible for example to cite the cauliflower mosaic virus promoter 35S as relatively strong promoter, compared to that for example originating from the the nos gene, these two promoters being more particularly used in the field of plant biotechnology. There thus exists a need for new promoters that are able to overcome the disadvantages described above of the application of the promoters known today.

One attempt at solving this problem has been reported in PCT application published under the number WO 97/48819, which describes promoters derived from the cassava vein mosaic virus (CsVMV), all of which comprise a portion of a nucleic acid sequence having 18 sequential nucleotides of which the homology to a reference sequence cited in the application is at least 80%. The expressions used in the present description and claims have the following meaning unless indicated otherwise:

"nucleic acid" means DNA or RNA;

"nucleic acid sequence" means a single or double stranded oligomer or polymer, of nucleotide bases read from the 5' end towards the 3' end, and comprises self-replicating plasmids, genes, DNA or RNA polymers, infectious or non-infectious, and functional or non-functional DNA or RNA. In the nucleotide notation used in the present application, and unless otherwise indicated, the left end of a single stranded nucleotide sequence simple is the 5' end;

"derived nucleic acid sequence" means that the sequence derives directly or indirectly from the sequence to which it refers, for example by substitution, deletion, addition, mutation, fragmentation, and/or synthesis of one or more nucleotides;

"promoter" or "promoter nucleic acid sequence" means a region of nucleic acid upstream of the start codon for translation which is directly implicated in the recognition and binding of RNA polymerase and other proteins necessary for transcription;

"plant promoter" is a promoter capable of initiating transcription in plant cells;

"constitutive promoter" is a promoter capable of expressing nucleic acid sequences operably linked thereto, in all or substantially all of the tissues of the host organism throughout the entire development of said organism;

"tissue specific promoter" is a promoter capable of selectively expressing, nucleic acid sequences operably linked to said promoter, in certain specific tissues of the host organism;

"operably linked to" means the linking of the promoter, to the nucleic acid sequence or gene, coding for a polypeptide to be produced, such that the promoter positively drives transcription of said linked nucleic acid sequence. It should be understood that the promoter sequence also includes transcribed sequences situated between the transcription initiation site and the translation start codon;

"expression cassette" means nucleotide sequences capable of directing the expression of a nucleic acid sequence, or a gene, coding for a polypeptide to be produced in a host organism compatible with such sequences. Such expression cassettes comprise at least one promoter and a transcription terminator signal, and optionally other factors necessary or useful for expression;

"vector" means expression systems, for example projectiles coated with DNA, nucleic acid based transit vehicles, nucleic acid molecules adapted for delivery of nucleic acid, and circular self-replicating autonomous DNA, for example plasmids, cosmids, phagemids, etc. If a recombinant micro-organism or cell culture is described as a host for an expression vector, this can also include circular extrachromosomal DNA (such as for example mitochondrial or chloroplast DNA), where DNA has been integrated into the chromosome(s) of the host(s), the vector either being stably replicated with the cells during mitosis as an autonomous structure, integrated into the host genome, or maintained in the nucleus or the cytoplasm of the host;

"plasmid" means a molecule of circular autonomous DNA capable of replication within a cell, and comprises both plasmids called "expression plasmids" and plasmids called "non-expression plasmids". If a recombinant micro-organism or cell culture is described in the present application as the host to an "expression plasmid", this means both molecules of circular extrachromosomal DNA and DNA having been integrated into the host chromosome. If the plasmid is maintained in a cell host, the plasmid is either stably replicated with the cells during mitosis as an autonomous structure, or integrated into the host genome;

"heterologous sequence" or "heterologous nucleic acid sequence" means a sequence originating from a source, or a species, that is foreign to its natural environment, or where it comes from the same environment, has been modified with respect to its original native form. The modification of the nucleic acid sequence can occur for example by treating the nucleic acid with a restriction enzyme to generate a nucleic acid fragment capable of being operably linked to a promoter. The modification can also be carried out using techniques such as site specific or site directed mutagenesis;

"box" means a nucleic acid sequence to which a regulatory function is attributed;

"like" means that the box and/or nucleic acid sequence to which the term refers, comprises a certain sequence identically or consensus with a known reference box and/or nucleic acid sequence, and preferably of at least 50% sequence identically, even more preferably a sequence identically of at least 75%, and most preferably a sequence identically of at least 90% with the reference sequence. The percentage of sequence identically is calculated on the basis of a comparison window of at least 6 contiguous nucleotide bases. The determination of a comparison window can be made by using sequence alignment algorithms in order to determine an homology with a reference sequence, for example the local homology algorithm, the homology alignment algorithm, and the similitude search algorithm, these algorithms also existing in electronic or computerised form, under the names GAP, BESTFIT, FASTA et TFASTA. The percentage of sequence identicality is obtained by comparing the reference sequence with the box and/or nucleic acid sequence;

"situated" means the position on a nucleic acid sequence of an identified element, such as a "box", a restriction enzyme site, or a codon having a particular function. The position given is indicated with a number that refers to the position of the start of the element in the nucleic acid sequence, in the reading from direction of the latter, that is to say, most frequently, and unless otherwise indicated from 5' to 3';

"transgenic plant" means a plant having been obtained using genetic manipulation techniques, and covers whole plants obtained thereby, their progeny, as well as vital plant organs, for example roots, stems and leaves, obtained using these techniques. The transgenic plants according to the present invention can have different levels of ploidy, and can in particular be polyploid, diploid, and haploid;

"propagule" means a structured or unstructured collection or assembly or association of plant cells, from which it is possible to regenerate a whole plant, for example explants, calli, stems, leaves, roots, cuttings, and even seeds.

The applicant of the present invention has taken a different approach to that taken by the applicant of the previously discussed PCT patent application. Indeed, the present applicant has serendipitously succeeded in producing chimeric promoters capable of satisfying and fulfilling the need described previously, and especially capable of increasing the rate of expression of a gene or nucleic acid sequence coding for a polypeptide to be produced, in a host cell, and more particularly in a plant cell or regenerated plant, with respect to the existing promoters most often used. Furthermore, the applicant has also succeeded in producing a complete family of promoters in order to be able to choose the promoter most suited to the envisaged task or application and the environment in which it will be put to work, and thus making it possible to control to a certain extent, the expression rate of a gene to be expressed coding for a polypeptide to be produced.

Consequently, one of the objects of the present invention is a chimeric expression promoter comprising at least one nucleic acid sequence, derived from a first plant promoter comprising a plant vascular expression promoter region, said plant vascular expression promoter region being replaced with a nucleic acid sequence derived from a second plant promoter and comprising a plant green tissue expression promoter region.

Preferably, the first plant promoter originates from the Commelina Yellow Mottle Virus (CoYMV) and the second plant promoter originates from the Cassava Vein Mosaic Virus (CsVMV).

Even more preferably, the promoter nucleic acid sequences originate from the intergenic regions of the first and second promoters.

In a particularly preferred embodiment, the chimeric expression promoter comprises at least a part of a nucleic acid sequence identified under the number SEQ.ID01 fused to at least a part of of a nucleic acid sequence identified under the number SEQ.ID02.

In an even more preferred embodiment, the chimeric promoter according to the invention is selected from the group consisting of the nucleic acid sequences identified under the numbers SEQ.ID03, SEQ.ID04, SEQ.ID05, SEQ.ID06 and SEQ.ID07.

According to another object of the present invention, the applicant has discovered that it was possible to produce particularly active chimeric expression promoters by starting from a base promoter of viral origin, of which a part consists of an exogenic element that is capable of promoting plant green tissue expression (GT). Preferably, the exogenic GT promoter element is also of viral origin. Furthermore, and according to a preferred embodiment of this aspect of the invention, the promoter of viral origin originates from the Commelina Yellow Mottle Virus (CoYMV).

Preferably, the exogenic promoter element originates from the Cassava Vein Mosaic Virus (CsVMV). Even more preferably, the exogenic GT element replaces the endogenic element capable of promoting vascular tissue expression (VT) of the promoter of viral origin.

According to a preferred embodiment of the previously defined objects of the invention recited above, the chimeric promoters further comprise at least one "endosperm like" box, and more preferably from 4 to 10 "endosperm like" boxes, and most preferably 6 "endosperm like" boxes.

According to another preferred embodiment, the promoters further comprise at least one "as1 like" box operably linked to the plant green tissue GT promoter element.

According to yet another preferred embodiment, the promoters of the present invention comprise at least one "as1" box operably linked to the plant green tissue (GT) promoter element.

In another preferred embodiment, the promoters further comprise at least one "as2" box operably linked to the plant green tissue (GT) promoter element.

Preferably, the one or more of the "as1 like", "as1", and "as2" boxes are operably linked upstream or downstream of the plant green tissue expression GT promoter element.

Even more preferably, the one or more of the "as1 like", "as1", and "as2" boxes are operably linked in normal (5'>3') or inverse (3'>5') orientation.

Most preferably, the promoter comprises at least one "as2/as2/as2" box in normal (5'>3') or inverse (3'>5') orientation.

Preferably, the previously described promoter is selected from the group consisting of the nucleic acid sequences identified under the numbers SEQ.ID01, SEQ.ID02, SEQ.ID03, SEQ.ID04, SEQ.ID05, SEQ.ID06, SEQ.ID07, SEQ.ID19, SEQ.ID20, SEQ.ID21, SEQ.ID22, SEQ.ID.23, SEQ.ID24, and SEQ.ID25.

Another object of the present invention is an expression cassette comprising at least one nucleic acid sequence, derived from a first plant promoter comprising a plant vascular expression promoter region, said plant vascular expression promoter region being replaced with a nucleic acid sequence derived from a second plant promoter and comprising a plant green tissue expression promoter region, the promoter nucleic acid sequences being operably linked to a nucleic acid sequence, or gene, to be expressed coding for a polypeptide to be produced, the latter nucleic acid sequence or gene being operably linked to a transcription terminator nucleic acid sequence.

Preferably, and according to this embodiment, said first plant promoter originates from the Commelina Yellow Mottle Virus (CoYMV) and said second plant promoter originates from the Cassava Vein Mosaic Virus (CsVMV). Even more preferably, the expression cassette comprises at least a part of a nucleic acid sequence identified under the number SEQ.ID01 fused to at least a part of a nucleic acid sequence identified under the number SEQ.ID02.

Even more preferably, the nucleic acid sequence of the chimeric promoter of the expression cassette is selected from the group consisting of the sequences identified under the numbers SEQ.ID03, SEQ.ID04, SEQ.ID05, SEQ.ID06, SEQ.ID07, SEQ.ID19, SEQ.ID20, SEQ.ID21, SEQ.ID22, SEQ.ID.23, SEQ.ID24, and SEQ.ID25.

In accordance with another object of the present invention, there is provided an isolated promoter nucleic acid sequence, selected from the group consisting of the sequences identified under the numbers SEQ.ID03, SEQ.ID04, SEQ.ID05, SEQ.ID06, SEQ.ID07, SEQ.ID19, SEQ.ID20, SEQ.ID21, SEQ.ID22, SEQ.ID.23, SEQ.ID24, and SEQ.ID25.

Yet another object of the invention relates to desoxynucleotide building blocks for the production of promoters or promoter nucleic acid sequences as defined above. These building blocks can be:

"directional" building blocks, that is to say sequences that read in the same direction as the reading frame of the final promoter sequence, usually from the 5' end to the 3' end; and/or "guide" blocks, that is to say sequences of whose ends comprise nucleotide bases that overlap with the ends of the directional building blocks.

In this way, and preferably, the directional building block corresponds to at least one sequence selected from the group consisting of the sequences identified under the numbers SEQ.ID08, SEQ.ID09, SEQ.ID10, SEQ.ID11, SEQ.ID13, and SEQ.ID14.

Moreover, it is preferred to use desoxynucleotide "guide" corresponding to at least one sequence selected from the group consisting of the sequences identified under the numbers SEQ.ID15, SEQ.ID16, SEQ.ID17, and SEQ.ID18.

Yet another object of the present invention is a vector comprising a promoter, or a promoter nucleic acid sequence, capable of initiating transcription of a nucleic acid sequence, or gene, coding form a polypeptide to be produced, wherein the promoter or promoter nucleic acid sequence corresponds to a chimeric expression promoter or to a promoter nucleic acid sequence as described previously above.

Preferably, the vector is selected from the group consisting of the binary vectors pMRT1152, pMRT1171, pMRT1172, pMRT1185, pMRT1186, pMRT1187, pMRT1188, pMRT1182, pMRT1245, pMRT1246, pMRT1247, pMRT1248, pMRT1249, pMRT1250, pMRT1251, pMRT1252, pMRT1253 and pMRT1254.

Finally, another object of the present invention is a process for the manufacture of a chimeric expression promoter or an isolated promoter nucleic acid sequence as described previously, wherein said process comprises the steps consisting of:

carrying out a ligation chain reaction, called LCR, to produce single stranded continuous DNA from at least one desoxynucleotide building block selected from the group consisting of the "directional" desoxynucleotide building blocks S1, S2, S3, S4, S5, S6, and S7 identified under the numbers SEQ.ID08, SEQ.ID09, SEQ.ID10, SEQ.ID11, SEQ.ID12, SEQ.ID13 and SEQ.ID14 respectively, and at least one "guide" desoxynucleotide building block for said promoter nucleic acid sequence or promoter selected from the group consisting of the guide desoxynucleotides G1, G2, G3 and G4 identified under the numbers SEQ.ID15, SEQ.ID16, SEQ.ID17 et SEQ.ID18 respectively;

carrying out PCR amplification on the single stranded DNA obtained from the previous step to produce a double stranded DNA corresponding to the chimeric expression promoter or the promoter nucleic acid sequence;

optionally isolating the promoter of promoter nucleic acid sequence.

Advantageously, and preferably, the desoxynucleotide building blocks are phosphorylated before ligation. Even more preferably, the ligation is carried out in the presence of at least one DNA ligase in a thermocycle, under the following conditions:

a cycle of about one minute at about 94° C.;

eight identical cycles, each one consisting of the following steps:

one minute at 65° C., one minute at 57° C., one minute at 52° C., one minute at 48° C., one minute at 43° C. and ten minutes at 37° C.

Yet another object of the present invention is a transgenic plant having stably integrated into its genome at least one promoter or at least one promoter nucleic acid sequence as defined previously. Preferably, the transgenic plant is selected from dicotyledonous species, and preferably potato, tobacco, cotton, lettuce, tomato, melon, cucumber, pea, rape, canola, beetroot, or sunflower, or from monocotyledonous species, and preferably wheat, barley, oat, rice, or corn.

Yet still another object of the present invention, is a propagule of a transgenic plant as defined previously, preferably the propagule is a seed.

According to the present invention, another object is a cell containing a promoter or promoter nucleic acid sequence as defined above, and preferably, the cell is a plant cell.

According to another object of the present invention, a method of expression of a nucleic acid sequence, or gene, is provided, that codes for a polypeptide to be produced, by the cell, wherein the method comprises the steps consisting of:

transforming a cell with a vector comprising at least one promoter or at least one promoter nucleic acid sequence as defined previously;

culturing the cell under conditions enabling expression of the nucleic acid sequence, or gene, coding for said polypeptide and production thereof. Preferably, the cell is a prokaryotic or eukaryotic cell, and more preferably is selected from the group consisting of microbial cells, algal and microalgal cells, fungal cells, insect cells, animal cells, mammalian and human cells, and plant cells, and most preferably is a plant cell.

According to yet another object of the present invention, a method of manufacture is supplied for manufacturing a transgenic plant or a propagule wherein the method comprises the steps consisting of:

transforming a plant cell with a vector comprising at least one promoter or at least one promoter nucleic acid sequence as defined previously;

selecting the plant cell having integrated the promoter or promoter nucleic acid sequence;

propagated the selected and transformed plant cell, by culture, or by regeneration of whole chimeric or transgenic plants.

BRIEF DESCRIPTION OF THE FIGURES

The invention will be better understood through the following detailed description of one or more preferred embodiments, given purely as non-limiting examples, and with referral to the annexed drawing in which:

In FIG. 1, the construction concerned contains the reporter gene coding for [beta ]-glucuronidase in the total absence of any promoter sequence as such, and thus useful as a negative control.

FIG. 2 schematically represents a construct containing the [beta]-glucuronidase gene under the control of the CaMV double 35S promoter, useful as a strong reference control;

FIG. 3 represents a construct useful as an internal reference for the transient expression experiments, and includes the reporter gene coding for a luciferase under the control of the CaMV 35S promoter;

the dark disk-shaped symbols represent the green tissue expression specific element;

the small white parallelepiped symbols represent the "endosperm like" boxes;

the small and large black hatched parallelepipeds represent respectively the "as-2" and "as-1" boxes from the CaMV promoter.

Figure 1:
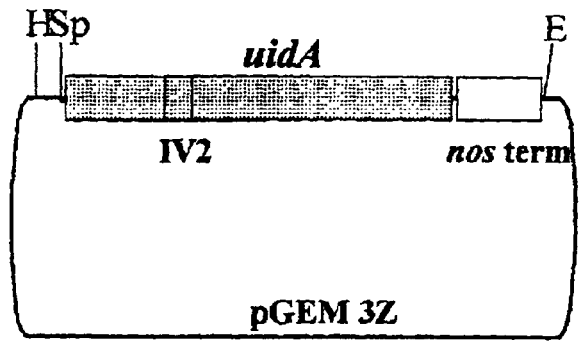
FIGS. 1, 2, and 3 schematically represent the structures of the comparative reference constructs, enabling a comparison of the chimeric promoters of the present invention with those already known and used.
Figure 2:
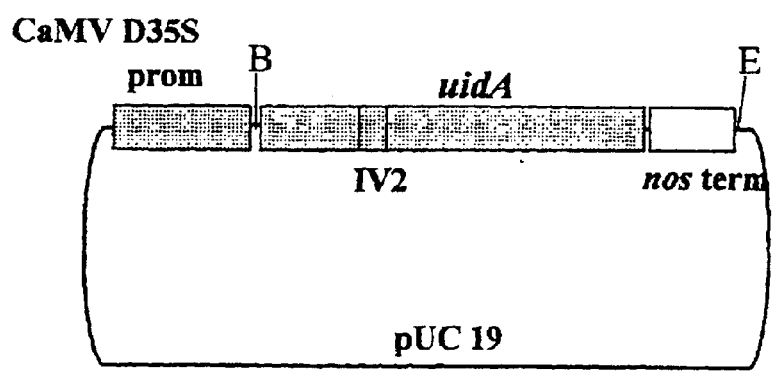
Figure 3:
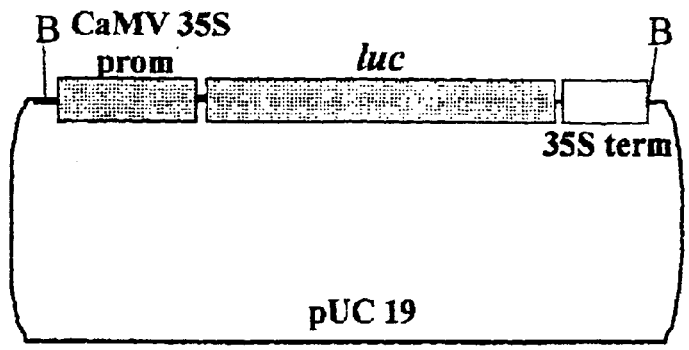
Figure 4:
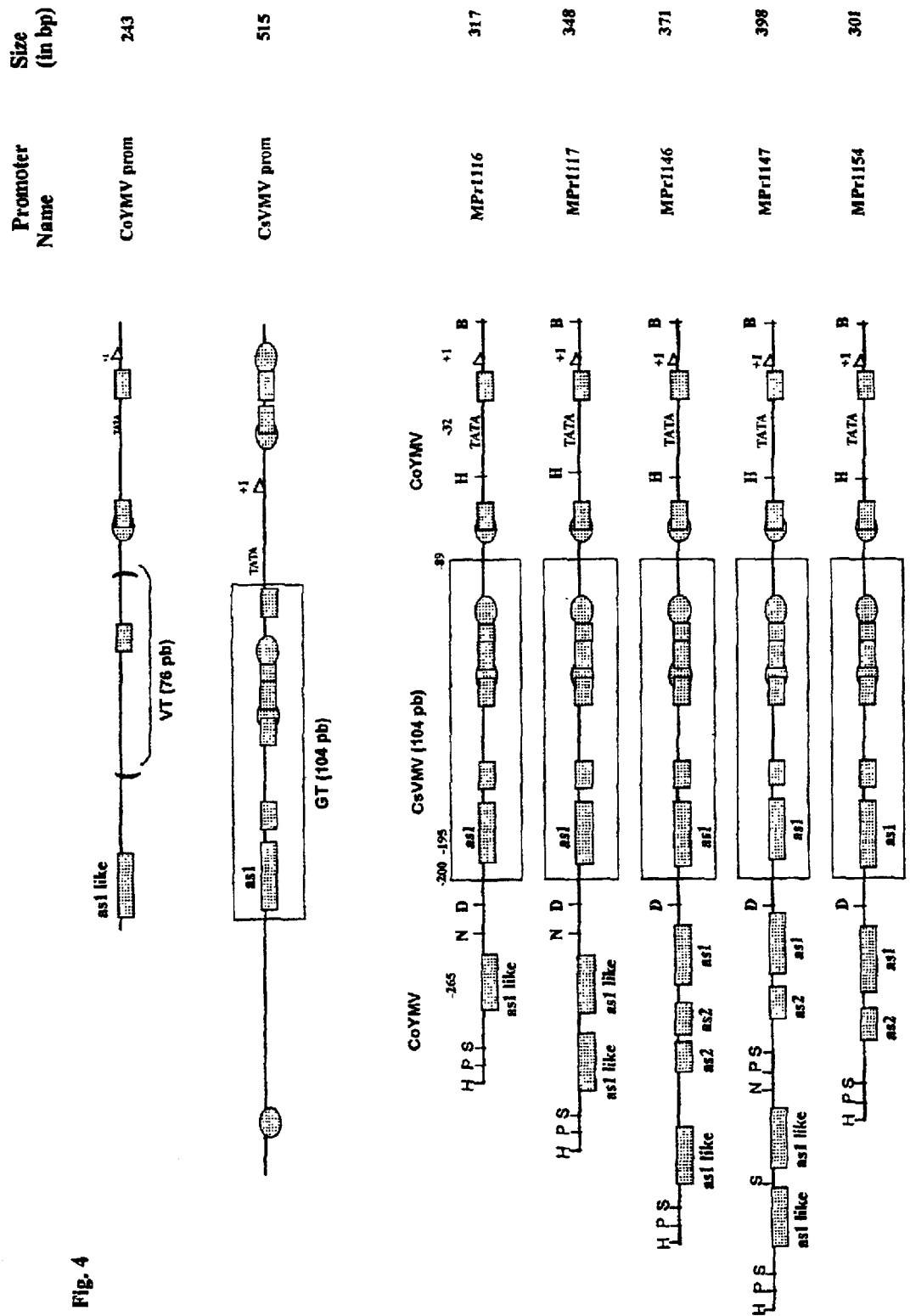
FIG. 4 schematically represents the structure of several preferred embodiments of chimeric promoters produced in accordance with the present invention. The chimeric promoters MPr1116 and MPr1117 were obtained using the technique called 1b-PCR. MPr1146 and MPr1147 were obtained by cloning the activator elements as1 and as2 from the CaMV promoter at the restriction enzyme site DraIII. The promoter MPr1154 was obtained through deletion of the two "as-1 like" sequences from the CoYMV promoter present in the 5' region of MPr1147. All of these promoters were cloned at the restriction sites PstI and BamHI into the vector pMRT1144 in order to obtain transcriptional fusion with the reporter gene uidA.
Figure 5:
FIG. 5 represents histochemical staining of tobacco leaves transformed with different promoters in accordance with the present invention. The tobacco leaves were transformed by a biolistic method using a gene gun sold under the tradename BIORAD PDS1000/HE, under the following conditions: split rupture disks at 900 psi, 2 μg of DNA bombarded over two successive firings, projectiles consisting of gold beads or spheres of about 1 μm in diameter, plant material positioned at 6 then 9 cm from the macrocarrier. After bombardment, the leaves were incubated in the dark in a culture chamber for 48 hours to enable expression of the reporter gene. The leaves were then incubated in a 0.1 M phosphate buffer containing 2 mg/ml of X-Glu at 37° C. for 24 to 48 hours, then bleached in a 70% ethanol bath.
Figure 5:
Figure 5:
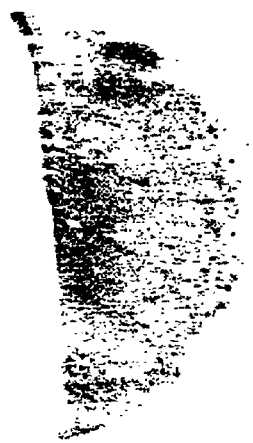
Figure 5:
Figure 5:
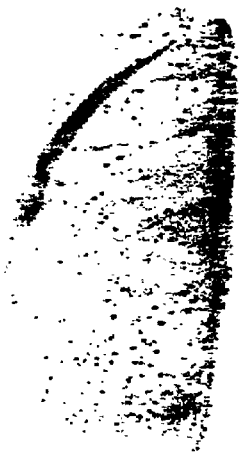
Figure 6:
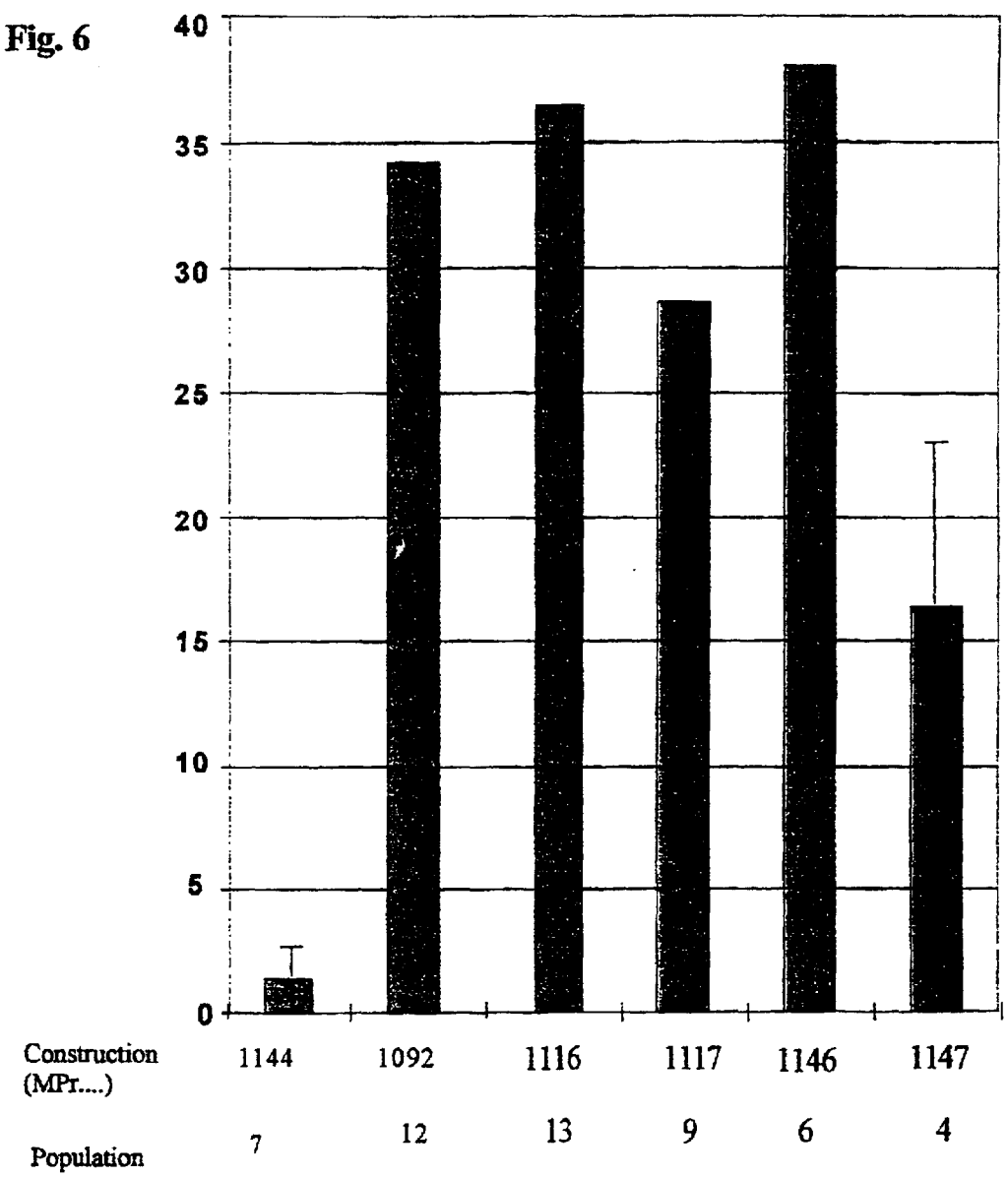
FIG. 6 represents a graph comparing the relative promoter activity of the different constructs after transient expression in tobacco leaves. Three days after bombardment the leaves were ground then the crude extract clarified by centrifugation. The β-glucuronidase and luciferase activities were measured using fluorimetric methods on crude extract aliquots, then the ratio of GUS activity/LUC activity was determined. The histograms correspond to the average of the ratios for a given construct+/−standard mean error.
Figure 7:
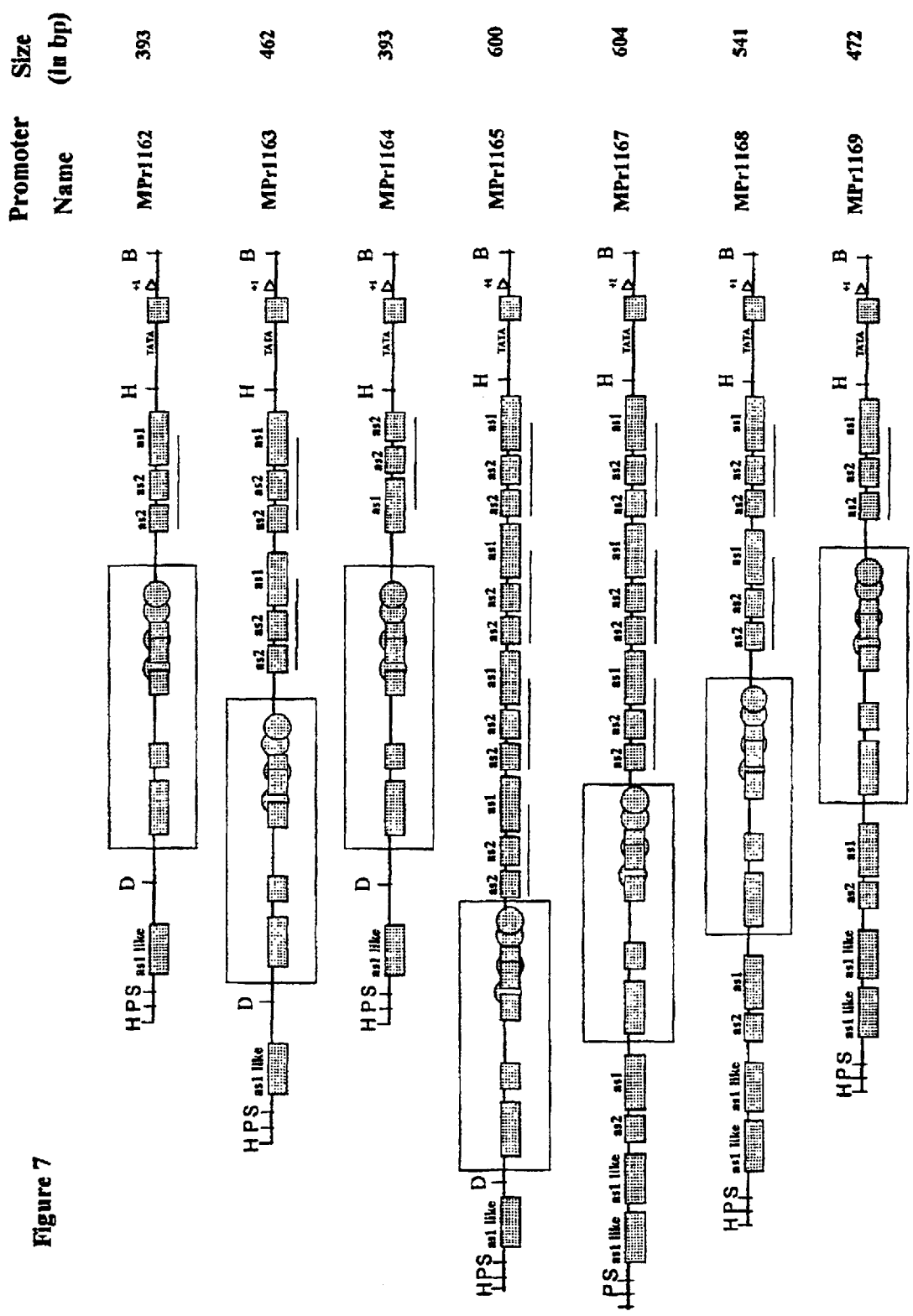
FIG. 7 schematically represents other preferred embodiments of chimeric promoters according to the present invention, where.
Figure 8:
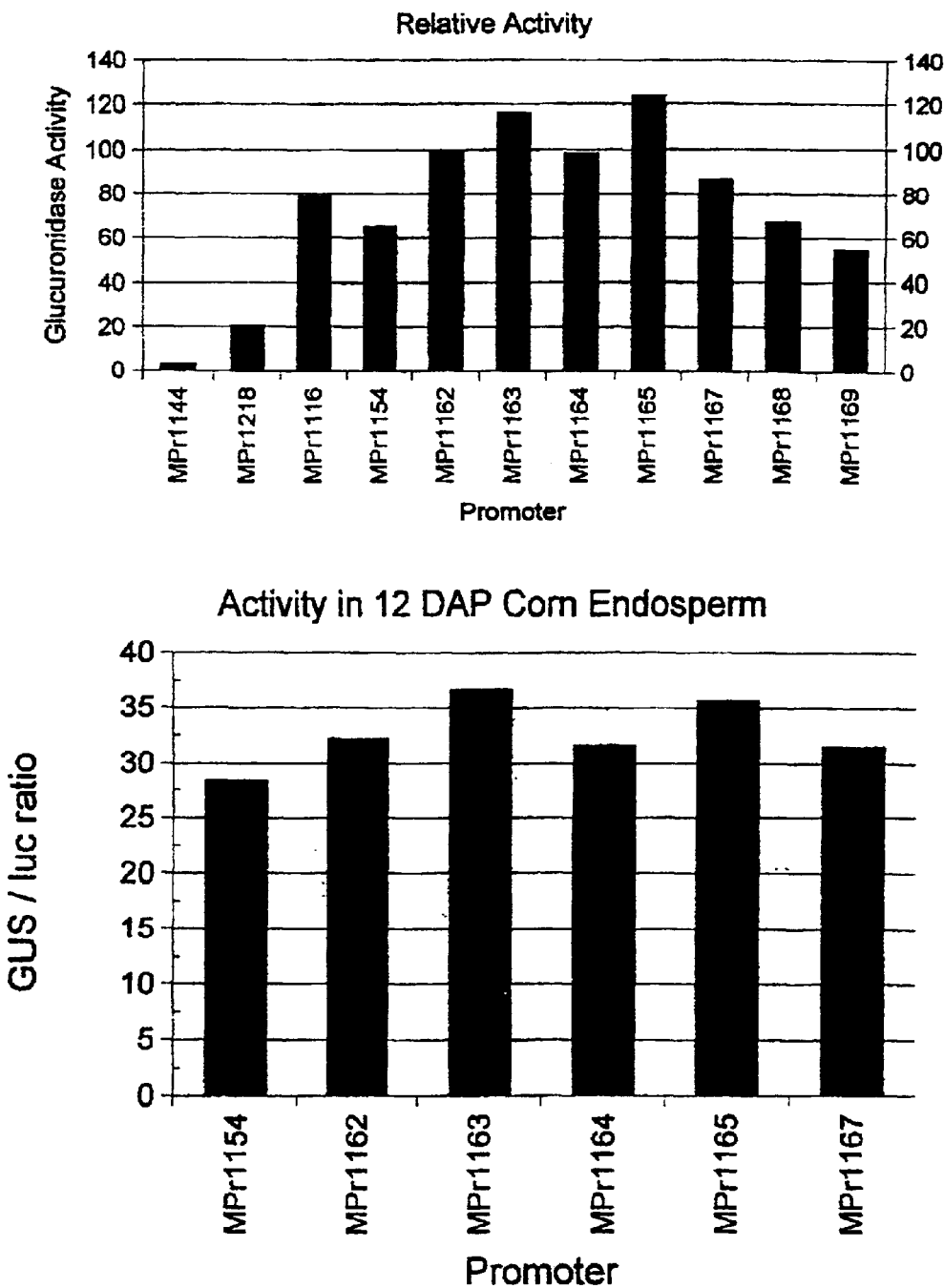
Figure 10:
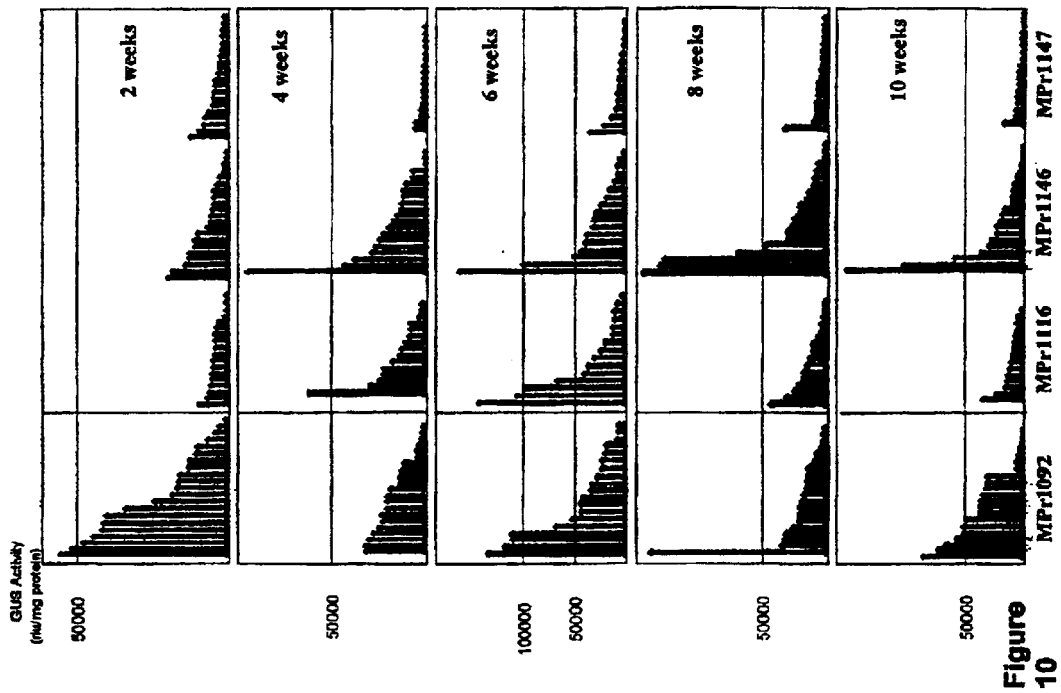
Figure 9:
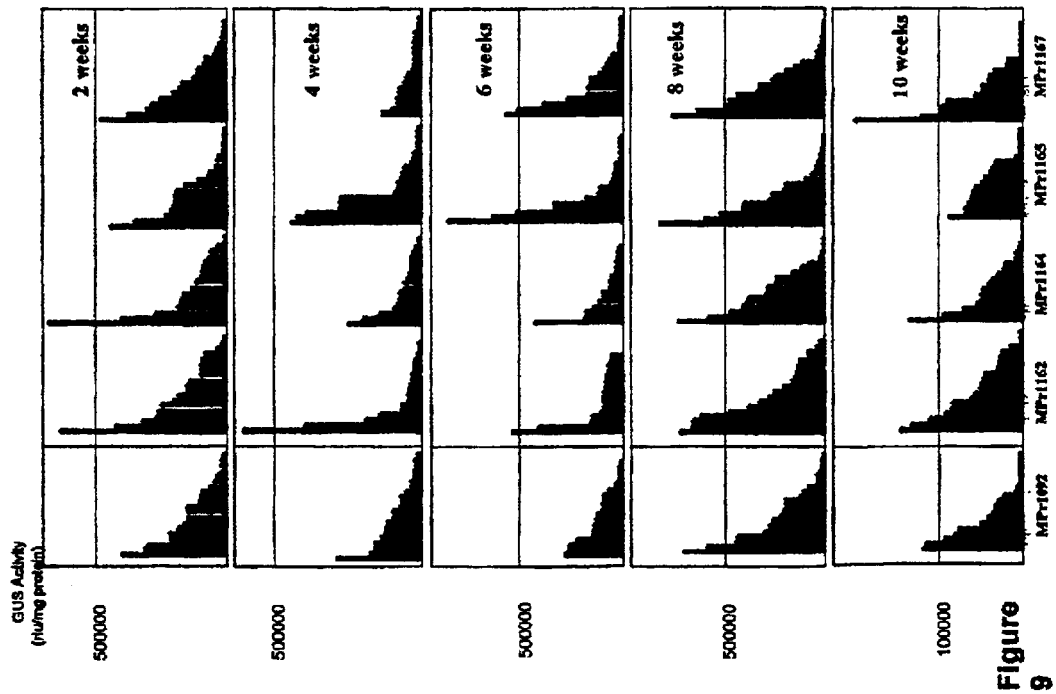

FIG. 8 represents a comparison of the relative activity of the different promoters of the invention in transient expression experiments in corn albumen, where the β-glucuronidase and luciferase activities were measured by fluorimetry on an aliquot of crude extract. The histograms correspond to the average for a given construction+/− standard mean error;

FIG. 9 represents a comparison of the relative activity of the chimeric promoters MPr1116, MPr1146, MPr1167 and reference promoter MPr1092, evaluated in stable tobacco expression. Samples were taken from each primary transformant at 2, 4, 6, 8, and 10 weeks after transfer of the plants into the greenhouse. The β-glucuronidase activity was measured on each sample and weighted in relation to the total quantity of total protein. For each series of transformants, at a given time, the activities are classed in decreasing order and compared;

FIG. 10 represents a comparison of the relative activity of the chimeric promoters MPr1162, MPr1164, MPr1165, MPr1167 and the reference promoter MPr1092, evaluated in stable tobacco expression. Samples were taken from each primary transformant at 2, 4, 6, 8, and 10 weeks after transfer to the greenhouse. The β-glucuronidase was measured on each sample and weighted in relation to the total quantity of protein. For each series of transformants, at a given times, the activities were classed in decreasing order and compared.

In the various figures, certain terms have the following meanings:
uidA=the sequence coding for β-glucuronidase;
IV2=the patatin gene intron;
nos term=the terminator from the Nopaline Synthase gene;
35S term=the RNA 35S CaMV terminator;
CaMV=the cauliflower mosaic virus;
as-1=activating sequence 1 from the CaMV 35S promoter;
as-2=activating sequence 2 from the CaMV 35S promoter;
B=the endonuclease restriction site BamHI;
E=the endonuclease restriction site EcoRI;
H=the endonuclease restriction site HindIII;
P=the endonuclease restriction site PstI;
Sp=the endonuclease restriction site SphI.
D=the endonuclease restriction site DraIII;
N=the endonuclease restriction site NdeI;
S=the endonuclease restriction site SpeI;
CoYMV=the Commelina Yellow Mottle Virus;
CsVMV=the Cassava Vein Mosaic Virus;
TATA=the TATA box;
+1=the transcription initiation site;
"like" means that the sequence is not 100% homologous to the sequence to which it refers, as defined previously.

EXAMPLES

Examples 1

Comparative Constructs (Controls)

In order to enable the comparison between the chimeric promoters of the present invention, and those known and currently used, the uidA gene coding for β-glucuronidase (Jefferson et al., 1986) and containing the intron IV2 sequence from the potato patatin gene ST-LS1 (Vancanneyt et al., 1990) (uidA-IV2) was placed under the control of one of the promoters and the terminator from the nopaline synthase gene (nos term) from *Agrobacterium tumefaciens* into the plasmid pGEM3Z commercialised by Promega Corp. (Madison, USA).

1.1 Construction of Negative Control pMRT1144.

In order to facilitate cloning, a plasmid derived from pGEM3Z, containing only the sequences "uidA-IV2/nos term" and lacking any promoter sequence was produced. This plasmid was designated pMRT1144 and served as the negative control (FIG. I).

In order to insert the uidA/nos term sequence into pGEM3Z, the uidA sequence under the control of the entire promoter from the pea plastocyanin gene and the nopaline synthase terminator, were isolated from 5 μg of plasmid pGA492-PpetE. This plasmid had been obtained by cloning, into the plasmid pGA492-Pem2-uidA, the petE promoter originating from the pea plastocyanin gene from the plasmid pKHn2 (Pwee et Gray, 1993) instead of the em2 promoter (Gaubier et al., 1993), originating from the plasmid bp I221-Pem2. The plasmid bp I221-Pem2 was digested with 20 units of each of the enzymes HindIII and EcoRI for 1 hour at 37° C. Then, the expression cassette "Pem2/uidA/nos term" was separated by electrophoresis on 0.8% agarose gel, electroeluted, precipitated it the presence of 1/10 volume 3M sodium acetate pH 4.8 and 2.5 volumes of absolute ethanol at −80° C. for 30 minutes, centrifuged at 12000 g for 30 min, washed in 70% ethanol, dried, resuspended in water and inserted at the HindIII and EcoRI sites of the plasmid pGA492 (An, 1986) previously digested by these two enzymes for 1 h at 37° C., precipitated in the presence of 1/10 volume 3M sodium acetate pH 4.8 and 2.5 volumes absolute ethanol at −80° C. for 30 min, centrifuged at 12000 g for 30 min, washed in 70% ethanol, dried and then resuspended in water. Ligation was carried out in the presence of 1.0 µl T4 10×DNA ligase buffer (Amersham) and 2.5 unites of T4 DNA ligase (Amersham) at 14° C. for 16 h.

Previously prepared viable and competent *Escherichia coli* DH5α, bacteria were transformed (Hannahan, 1983). The plasmid DNA of the obtained clones, selected on Luria-Bertani media (LB, bactotryptone 10 g/l, yeast extract 5 g/l, NaCl 10 g/l, Agar 15 g/l) supplemented with tetracycline (12 mg/l), was extracted according to the alkaline lysis method (Birnboim et Doly, 1983) and analysed by enzymatic digestion.

Starting from the obtained pGA492-Pem2-uidA plasmid, the promoter Pem2 was deleted by double digestion with HindIII and XbaI. The plasmid fragment was separated by electrophoresis on 0.8% agarose gel, electroeluted, precipitated in the presence of 1/10 volume 3M sodium acetate pH 4.8 and 2.5 volumes absolute ethanol at −80° C. for 30 min, centrifuged at 12000 g for 30 min, washed in 70% ethanol, dried, subjected to a Klenow fragment of DNA polymérase I (New England Biolabs) for 30 min at 37° C. according to the manufacturer's recommendations. Then, it was deproteinized by extraction a volume of phenol, then a volume of phenol: chloroform:isoamyl alcohol (25:24:1 v/v/v) and finally a volume of chloroform:isoamyl alcohol (24:1 v/v), precipitated in the presence of 1/10 volume 3M sodium acetate pH 4,8 and 2,5 volumes absolute ethanol at −80° C. for 30 min, then centrifuged at 12000 g for 30 min, washed in 70% ethanol, dried, resuspended in water. Then, it was dephosphorylated for 1 h at 37° C. using 10 units of calf intestine alkaline phosphatase (Boehringer Mannheim) according to the manufacturer's recommendations, deproteinized by extraction with a volume of phenol, then a volume of phenol:chloroform:isoamyl alcohol (25:24:1 v/v/v) and finally a volume of chloroform:isoamyl alcohol (24:1 v/v), precipitated in the presence of 1/10 volume 3M sodium acetate pH 4.8 and 2.5 volumes absolute ethanol at −80° C. for 30 min then centrifuged at 12000 g for 30 min, washed in 70% ethanol, dried then resuspended in water. The resulting plasmid was designated pGA492ΔPem2.

In parallel, the promoter pete (818 bp) which corresponds to the promoter of the pea plastocyanin gene, was obtained from the plasmid pKHn2 by digestion with NcoI for 1 h at 37° C. The 828 bp promoter fragment was isolated on 0.8% agarose gel, electroeluted, precipitated in the presence of 1/10 volume 3M sodium acetate pH 4.8 and 2.5 volumes absolute ethanol at −80° C. for 30 min, centrifuged at 12000 g for 30 min, washed in 70% ethanol, dried, resuspended in water, then subjected to the action of 5 units of Mung Bean nuclease (New England Biolabs) for 30 min at 30° C. according to the manufacturer's recommendations, deproteinized by extraction with a volume of phenol, then a volume of phenol:chloroform:isoamyl alcohol (25:24:1 v/v/v) and finally a volume of chloroform:isoamyl alcohol (24:1 v/v), precipitated in the presence of 1/10 volume 3M sodium acetate pH 4.8 and 2.5 volumes absolute ethanol at −80° C. for 30 min then centrifuged at 12000 g for 30 min, washed in 70% ethanol, dried then resuspended in water. This promoter fragment was inserted into the plasmid pGA492ΔPem2, described above, in the presence of 1.0 µl T4 10×DNA ligase buffer (Amersham) and 2.5 units of T4 DNA ligase (Amersham) at 14° C. for 16 h. Previously prepared viable and competent *Escherichia coli* DH5α bacteria were transformed. The plasmid DNA of the obtained clones, selected on LB media supplemented with tetracycline (12 mg/l), was extracted according to the alkaline lysis method and analysed by enzymatic digestion. The resultant plasmid was designated pGA492-petE prom.

In order to isolate the expression cassette "petE prom/uidA/nos term", 5 µg of plasmid pGA492-petE prom were digested with PstI (site situated in the 5' region of the promoter of the pea plastocyanin gene) and EcoRI (site situated in the 3' region of the terminator sequence) for 1 h at 37° C., subjected to 0.8 agarose gel electrophoresis and purified on a QIAquick affinity column (Qiagen, Hilden, Germany) according to the recommendation of the supplier. Furthermore, 500 ng of the plasmid pGEM3Z were simultaneously digested for 1 h at 37° C. with EcoRI and PstI (restriction sites present in the multiple cloning site or polylinker), subjected to 0.8% agarose gel electrophoresis, then purified on a QIAquick affinity column.

The ligation was carried out with 50 ng of vector pGEM3Z-PstI/EcoRI and 50 ng of the expression cassette petE prom/uidA/nos term for 1 night at 18° C. in a reaction volume of 12 µl in the presence of 1.2 µl T4 10×DNA ligase buffer (New England Biolabs) and 400 units of T4 DNA ligase (New England Biolabs). Previously prepared *Escherichia coli* DH5α bacteria were transformed with the ligation reaction mixture. The plasmid DNA of the obtained clones, selected on LB media supplemented with ampicillin (50 mg/l), was extracted according to the alkaline lysis method and analysed by enzymatic digestion. The plasmid obtained was designated pGEM3Z-petE prom.

In order to insert the 192 bp IV2 intron from the potato patatin gene into the coding uidA sequence, an internal portion of this gene (fragment SnaBI/BstBI of 710 bp in pGEM3Z-petE prom) was excised then replaced with the equivalent sequence containing the IV2 intron (fragment SnaBI/BstBI of 902 bp). In order to achieve this, the plasmid pGEM3Z-petE prom was digested for 1 h at 37° C. with SnaBI (restriction site situated at position +383 bp downstream of the initiator ATG codon of the uidA gene) then for 1 h at 65° C. with BstBI (site situated at position +1093 bp). The plasmid deleted of this 710 bp fragment was isolated by 0.8% gel agarose electrophoresis, then purified on a QIAquick affinity column. The fragment BstBI/SnaBI of 902 bp corresponding to the IV2 intron sequence followed by the uidA sequence stretching from position +383 to +1093 bp, was isolated and purified from the plasmid pSCV1.2-GI. This plasmid derives from the plasmid pSCV1.2 which in turn derives from the plasmid pSCV1 constructed by G. A. Edwards in 1990 according to the usual cloning methods. The binary plasmid pSCV1.2 was obtained through cloning of the fragment HindIII bearing the expression cassette "35S prom/nptII/nos term" (Fromm et al., 1986) at the HindIII site of pSCV1. The expression cassette "35S prom/GUS-IV2/35S term" was obtained by digesting the plasmid p35S GUS INT with HindIII for 1 h at 37° C. as described by Vancanneyt et al. (1990). The DNA fragment corresponding to the expression cassette was isolated on 0.8% agarose gel, electroeluted then precipitated in the presence of 1/10 volume 3M sodium acetate pH 4.8 and 2.5 volumes absolute ethanol at −80° C. for 30 min then centrifuged at 12000 g for 30 min, washed in 70% ethanol, dried and resuspended in water. The 5' protruding ends of this fragment were blunted by the action of the DNA polymerase I Klenow fragment (New England Biolabs) for 30 min at 37° C. according to the manufacturer's recommendations, and the fragment was deproteinized by extraction with a volume of phenol, then a volume of phenol:chloroform:isoamyl alcohol (25:24:1 v/v/v) and finally a volume of chloroform:isoamyl alcohol (24:1 v/v), precipitated in the presence of 1/10 volume 3M sodium acetate pH 4,8 and 2,5 volumes absolute ethanol at −80° C. for 30 min then, centrifuged at 12000 g for 30 min, washed in 70% ethanol, dried and finally ligated with 20 ng of plasmid pSCV1.2, digested with SmaI for 1 h at 25° C., in the presence of 1.0 µl T4 10×DNA ligase buffer (Amersham) and 2.5 units of T4 DNA ligase (Amersham) at 14° C. for 16 h. Previously prepared competent and viable *Escherichia coli* DH5α bacteria were transformed. The plasmid DNA of the obtained clones, selected on LB media supplemented with ampicillin (50 mg/l), was extracted according to the alkaline lysis method and analysed by enzymatic digestion.

Five micrograms (5 µg) of the plasmid pSCV1.2-GI were digested for 1 h at 37° C. with SnaBI (restriction site situated at position +383 bp downstream of the initiator ATG codon of the gene uidA) then for 1 h at 65° C. with BstBI (site situated at position +1285 bp). The 902 bp fragment was isolated by 1.0% agarose gel electrophoresis, then purified on a QIAquick affinity column.

The ligation was carried out with 20 ng of vector pGEM3Z-petE prom BstBI/SnaBI and 80 ng of the 902 bp fragment BstBI/SnaBI, for 1 night at 18° C. in a reaction volume of 10 µl in the presence of 1.0 µl of T4 10×DNA ligase buffer (New England Biolabs) et 400 units of T4 DNA ligase (New England Biolabs). Previously prepared competent and viable *Escherichia coli* DH5α bacteria were transformed with half of the ligation reaction mixture. The plasmid DNA of the obtained clones, selected on LB media supplemented with ampicillin (50 mg/l), was extracted according to the alkaline lysis method and was analysed by enzymatic digestion. The plasmid obtained was designated pGEM3Z-petE prom/IV2.

In order to eliminate the promoter sequence corresponding to the 818 bp fragment (petE) from the plasmid pGEM3Z-petE prom/IV2, the latter was digested for 1 h at 37° C. with BamHI then, for 1 h at 37° C. with PstI, isolated by electrophoresis on 0.8% gel agarose, then purified on a QIAquick affinity column. The protruding 5' ends of this plasmid were blunted with Pfu DNA polymerase (Stratagene, La Jolla, USA) according to the supplier's recommendations. The ligation was carried out with 10 ng of thus modified plasmid for 1 night at 18° C. in a reaction volume of 12 µl, in the presence of 1.2 µl of T4 10×DNA ligase buffer (New England Biolabs) and 400 units of T4 DNA ligase (New England Biolabs). Previously prepared competent and viable *Escherichia coli* DH5α bacteria were transformed with half the reaction mixture of ligation. The plasmid DNA of the obtained clones, selected on LB media supplemented with ampicillin (50 mg/l), was extracted according to the alkaline lysis method, analysed by enzymatic digestion, et verified by sequencing according to the method described by Sanger et al. (1977). The plasmid obtained was designated pMRT1144 (FIG. I).

1.2. Construction of the Positive Control MPr1092.

In order to obtain a reference promoter sequence, the "double 35S" promoter from the cauliflower mosaic virus (CaMV D35S prom), was placed upstream of the sequence uidA-IV2/nos term. The plasmid pMRT1092 (FIG. I) resulted from the following cloning steps: First of all, the 192 bp IV2 intron from the potato patatin gene was inserted into the coding sequence uidA at position +383 bp as described in section 1.1. A one microgram amount (1 µg) of plasmid pBI221 (Clontech, Calif., USA) was digested for 1 h 30 at 37° C. with SnaBI then for 1 h 30 at 65° C. with BstBI. The plasmid deleted of the 710 bp fragment was isolated by 0.8% agarose gel electrophoresis, then purified on a QIAquick affinity column.

A twenty nanogram amount (20 ng) of the vector pBI221 BstBI/SnaBI and 80 ng of the 902 bp fragment BstBI/SnaBI originating from pSCV1.2-GI as described previously, were ligated for 1 night at 18° C. in a reaction volume of 10 µl, in the presence 1 µl of T4 10×DNA ligase buffer (New England Biolabs) and 400 units T4 DNA ligase (New England Biolabs). Previously prepared competent and viable *Escherichia coli* DH5α bacteria were transformed with half of the ligation reaction mixture. The DNA of the obtained clones, selected on LB media supplemented with ampicillin (50 mg/l), was extracted according to the alkaline lysis method and analysed by enzymatic digestion. The plasmid obtained was designated pBI221/uidA-IV2.

Next, the sequence of the simple 35S CaMV promoter present in the plasmid pBI221/uidA-IV2 was replaced with the sequence "CaMV D35S". In order to achieve this, the plasmid pBI221/uidA-IV2 was digested for 10 h 30 at 37° C. with 10 units of HindIII, then the sticky ends were blunted by the action of the Klenow fragment of DNA polymerase I (New England Biolabs) for 30 min at 37° C. according to the manufacturer's recommendations. After purification of the product of this reaction on a QIAquick affinity column, the DNA was digested for a night at 37° C. with 10 units of BamHI. The plasmid fragment, corresponding to the vector deleted of the 828 bp CaMV 35S promoter fragment, was isolated by 0.8% agarose gel electrophoresis, then purified on a QIAquick affinity column.

The CaMV D35S promoter was obtained from the plasmid pJIT163Δ. This plasmid derives from pJIT163 which in turn derives from the plasmid pJIT160 (Guérineau et Mullineaux, 1993). The plasmid pJIT163 possesses a ATG codon between the sites HindIII and SalI of the polylinker. In order to delete this ATG and obtain the plasmid pJIT163Δ, the plasmid DNA of pJIT163 was digested with HindIII and SalI, purified by 0.8% agarose gel electrophoresis electroeluted, precipitated in the presence of 1/10 volume 3M sodium acetate pH 4.8 and 2.5 volumes absolute ethanol at −80° C. for 30 min, centrifuged at 12000 g for 30 min, washed in 70% ethanol, dried, subjected to the action of the Klenow fragment of DNA polymerase I (New England Biolabs) for 30 min at 37° C. according to the manufacturer's recommendations, deproteinized by extraction with a volume of phenol, then a volume of phenol:chloroform:isoamyl alcohol (25:24:1 v/v/v) and finally a volume of chloroform:isoamyl alcohol (24:1 v/v), precipitated in the presence of 1/10 volume 3M sodium acetate pH 4.8 and 2.5 volumes absolute ethanol at −80° C. for 30 min, then centrifuged at 12000 g for 30 min, washed in 70% ethanol, dried and finally ligated in the presence of 1.0 µl of T4 10×DNA ligase buffer (Amersham) et 2.5 units T4 DNA ligase (Amersham) at 14° C. for 16 h. Previously prepared viable and competent *Escherichia coli* DH5α bacteria were transformed. The plasmid DNA of the obtained clones, selected on LB media supplemented with ampicillin (50 mg/l), was extracted according to the alkaline lysis method and analysed by enzymatic digestion.

Ten micrograms (10 μg) of the plasmid pJIT163Δ were digested for 10 h 30 at 37° C. with 10 units of KpnI (site situated in the 5' region of the promoter) then the sticky ends were blunted with the action of 6 units of T4 DNA polymerase (New England Biolabs) for 30 min at 37° C. according to the manufacturer's recommendations. After purification of the product of this reaction on a QIAquick affinity column, the DNA was digested for a night at 37° C. with 10 units of BamHI. The resulting 761 bp DNA fragment, corresponding to the D35S promoter was isolated by 1.0% agarose gel electrophoresis, then purified on a QIAquick affinity column.

The reaction mixture containing 10 ng of plasmid vector, 100 ng of the 761 bp fragment, 1.0 μl of T4 10×DNA ligase buffer (New England Biolabs) and 400 units T4 DNA ligase (New England Biolabs) was subjected to ligation in 10 ml for a night at 18° C. Previously prepared viable and competent *Escherichia coli* DH5α bacteria were transformed with half of the ligation reaction mixture. The plasmid DNA of the obtained clones, selected on LB media supplemented with ampicillin (50 mg/l), was extracted according to the alkaline lysis method and analysed by enzymatic digestion. The plasmid obtained was designated pMRT1092 (FIG. II).

1.3. Description of the Reference Plasmid pCaMV35Sluc.

The plasmid used as an internal reference for transient expression was pCaMV35Sluc (Torrent et al., 1997) which contains the expression cassette for the luciferase (luc) reporter gene under the control of the RNA CaMV 35S promoter and terminator (FIG. III).

Example 2
Construction of Chimeric Promoters Combining Elements from the CsVMV and CoYMV Promoters.

The entire promoter of the intergenic region of CoYMV corresponds to a sequence of 1038 bp stretching from position −1026 bp to position +12 bp (with respect to the 5' end of the CoYMV transcript, and previously identified as sequence EMBL X52938, by Medberry et al., 1992). A fragment of 243 bp of this whole promoter (Medberry and Olszewski, 1993) was retained for the construction of the chimeric promoters according to the present invention as identified in the sequence listing under SEQ.ID01.

On this 243 bp fragment, several potentially regulatory sequences have been putatively identified (from the 5' end in the direction of the 3' end, the positions of which are indicated in in base pairs (bp) with respect to the transcription initiation start point +1 as illustrated in FIG. IV:

an "as-1 like" box of 16 bp in length having a certain similarity to the activating sequence 1 (as-1) which is present in the CaMV 35S promoter, and stretching from position −226 bp to position −210 bp;
a 76 bp sequence responsible for the expression in vascular tissues (Medberry et al., 1992), stretching from position −161 bp to position −85 bp, and designated VT in FIG. IV;
a GTAA element specific to expression in green tissue situated at position −76 bp;
three "endosperm like" boxes having a certain similarity to the boxes responsible for specific expression in the endosperm of cereal plants, located at positions −118 bp, −77 bp and −20 bp;
a "TATA" box, at position −32 bp;
the start point of transcription +1 (position 1);
a 5' untranslated region (UTR) stretching from position +1 to position +12 bp.

The promoter of the intergenic region of CsVMV corresponds to a sequence of 515 bp stretching from position +7162 bp to position +7677 bp (previously identified as sequence EMBL U59751, Verdaguer et al., 1996). On this 515 bp fragment, identified in the sequence listing under SEQ.ID02, several potentially regulatory sequences have been putatively-identified (from the 5' end in the direction of the 3' end, the positions of which are indicated in base pairs (bp) with respect to the transcription initiation start point +1, as illustrated in FIG. IV):

a 104 bp sequence, reported as being responsible for conferring strong expression in green tissues and stretching from position −220 bp to position −116 bp, designated as GT in FIG. IV;
an "as-1 like" element of 16 bp in length, having a certain similarity to the activating sequence 1 (as-1) present in the CaMV 35S promoter, and stretching from position −219 bp to position −203 bp;
7 "GTAA" elements specific for the expression in green tissues and located at positions −437, −216, −144, −130, −116 bp, +16 and +63 bp;
7 "endosperm like" boxes having a certain similarity to the boxes responsible for specific expression in the endosperm of cereal plants, and located at positions −196, −145, −136, −130, −122, +14 and +31 bp;
a "TATA" box, at position −33 bp;
the initiation start point of transcription +1 (position +1);
a 5' untranslated region (UTR) stretching from position +1 to position 71 bp.

2.1. Construction of MPr1116.

The 104 bp sequence of CsVMV stretching from position −221 bp to position −116 bp (as referenced by the start point of initiation of transcription +1), bears 4 "endosperm like" boxes, four "GTAA" elements specific to expression in green tissues, and an as-1 type element, and is responsible for the expression in vascular tissues. The 76 bp region of CoYMV (stretching from position −160 bp to position −84 bp as identified in the sequence listing under the number SEQ.ID01), is responsible for the expression in vascular tissues.

The promoter MPr1116, as schematically illustrated in FIG. IV, was created by fusing the sequence of 104 bp of the promoter from the intergenic region of the CsVMV genome, identified in the sequence listing under SEQ.ID02, to the CoYMV sequence deleted of its 76 bp region, using the lb-PCR technique.

The single stranded continuous DNA was formed starting from the following "directional" desoxynucleotides:

- S1 = 5' CATGCTGCAGACTAGTATCCGCCGTCATCAATGACATCATCACAGTACTGAGGAGATGAATAGCT 3'   (SEQ.ID08)

- S2 = 5' AGCCATGACACTCTGTGCGAATATTGAAGACGTAAGCACTGACGACAACAATGAAAAGAA 3'   (SEQ.ID09)

- S3 = 5' GAAGATAAGGTCGGTGATTGTGAAAGAGACATAGAGGACACATGTAAGGTGGAAAATGTAAG 3'   (SEQ.ID10)

- S4 = 5' GGCGGAAAGTAACCTTATGCATTTGTAACTTGGTTACCCGGTATGCCGGTTCCCAAGCTTTAT 3'   (SEQ.ID11)

- S5 = 5' TTCCTTATTTAAGCACTTGTGTAGTAGCTTAGAAAACCAACACAACAACCTAGAGGATCCCCG 3'   (SEQ.ID12)

One hundred picomoles of desoxynucleotides S1, S2 and S3 were phosphorylated in the 5' region by the action of 15 units of kinase (Amersham) in the presence of 5 μl 10×kinase buffer (Amersham) and 500 picomoles of ATP (Sigma), for 30 minutes at 37° C. The phosphorylated oligodesoxynucleotides were purified by extraction with a volume of phenol, then a volume of phenol:chloroform:isoamyl alcohol (25:24:1 v/v/v) and finally a volume of chloroform:isoamyl alcohol (24:1 v/v), before being precipitated with of 1/10 volume 3M sodium acetate pH 4.8 et 2.5 volumes absolute ethanol at −80° C. for 20 min then centrifuged at 16060 g for 30 min. The precipitated oligodesoxynucleotides were washed in 70% ethanol, dried, then resuspended in water at a concentration of 10 pmol/μl.

In order to link the "directional" oligodesoxynucleotides, the following "guide" oligodesoxynucleotides were used:

```
- G1 = 5'
GACTCCTCTACTTATCGATCGGTACTGTGAGACA 3'    (SEQ.ID15)

- G2 = 5'
GCTGTTGTTACTTTTCTTCTTCTATTCCAGCCA 3'     (SEQ.ID16)

- G3 = 5'
ATTCCACCTTTTACATTCCCGCCTTTCATTG 3'       (SEQ.ID17)

- G4 = 5'
CAAGGGTTCGAAATAAAGGAATAAATTCGTGA 3'      (SEQ.ID18)
```

In order to carry out the LCR reaction, 10 pmol of the phosphorylated "directional" desoxynucleotides S1, S2, S3, S4, and S5 were ligated in the presence of 10 pmol of the "guide" desoxynucleotides G1, G2, G3 and G4, 5 μl 10×Taq DNA ligase buffer (New England Biolabs) and 40 units Taq DNA ligase (New England Biolabs). The ligation reaction was carried out in a GeneAmp PCR System 9700 thermocycle (Perkin Elmer, Norwalk, USA). It consisted of a cycle of 1 min at 94° C., and 8 identical cycles each consisting of the succession of the following steps: 1 min at 65° C., 1 min at 57° C., 1 min at 52° C., 1 min at 48° C., 1 min at 43° C., and finally 10 min at 37° C. Then the ligation reaction mixture was purified on a QIAquick column according to the supplier's recommendations.

Finally, PCR amplification of the single stranded DNA obtained was effected in a GeneAmp PCR System 9700 thermocycle in the presence of 100 pmol of each of the oligodesoxynucleotide probes 5' CATGCTGCAGACTAG-TATCC 3' (SEQ ID NO:26) and 5' CGGGGATCCTCTAG-GTTGT 3' (SEQ ID NO:27), 50 nmol of each of the dNTP, 10 μl of Vent 10×DNA polymerase buffer (New England Biolabs), and 2 units of DNA Vent polymerase (New England Biolabs). The DNA was denatured for 5 min at 94° C., subjected to 25 cycles each consisting of a 30 sec denaturing step at 95° C., of a 30 sec hybridisation step at 55° C., and a 45 sec elongation step at 72° C., and then elongation at 72° C. was continued for 5 min. The DNA fragments from the reaction mixture were digested for 45 min at 37° C. with 20 units of BamHI, then for 1 h at 37° C. with 20 units of PstI, and finally purified on a QIAquick column. They were inserted into the plasmid pGEM3Z-petE prom (described at section 1.2.) digested for 1 h at 37° C. with BamHI then for 1 h at 37° C. with PstI, subjected to 0.8% agarose gel electrophoresis, purified on a QIAquick affinity column, dephosphorylated for 1 h at 37° C. in the presence of 12 μl of 10×buffer 3 (New England Biolabs) and 5000 units of calf intestine alkaline phosphatase (CIP, New England Biolabs), and finally purified on a QIAquick affinity column. To carry out ligation, 25 ng of the plasmid treated as described above was contacted with 100 ng of the DNA fragments obtained from the PCR reactions, in the presence of 1.2 μl of T4 10×DNA ligase buffer (New England Biolabs) and 400 units of T4 DNA ligase (New England Biolabs) for 1 night at 18° C. Previously prepared *Escherichia coli* DH5α bacteria were transformed with half of the ligation reaction mixture. The DNA of the obtained clones, selected on LB media supplemented with ampicillin (50 mg/l), was extracted according to the alkaline lysis method, and analysed by enzymatic digestion and gene amplification using the desoxynucleotides 5' CATGCTGCAGACTAG-TATCC 3' (SEQ ID NO:26) selected on the promoter and 5' TTGATTTCACGGGTTGGG 3' (SEQ ID NO:28) selected on the uidA sequence. Two resulting plasmids pMRT1116 and pMRT1117 were sequenced. The plasmid pMRT1116 contains the promoter MPr1116 (SEQ.ID03), whereas the plasmid pMRT1117 bears the promoter MPr1117 (SEQ.ID04) which differs from MPr1116 by a duplication, in the 5' region of the chimeric promoter, of the "as-1 like" box and its immediate environment, the length of which is 33 bp, as well as the deletion of 3 bp at position −140, −25 and −24, and the replacement of a cytosine with a thymine at position −54 bp (as illustrated by FIG. IV).

2.2. Construction of the Promoter MPr1146:

The promoter MPr1146 (FIG. IV) was obtained by inserting the 58 bp sequence corresponding to a duplication of the as-2 element (Lam et Chua, 1989) and of the as-1 element (Lam et al., 1989) originating from the RNA 35S CaMV promoter at the restriction sites NheI and DraIII of MPr1116.

In order to achieve this, the plasmid pMRT1116 was digested for 1 h at 37° C. with 25 units of NheI, then for 1 h at 37° C. with 4 units of DraIII. The plasmid thus digested was isolated on 0.8% agarose gel, purified on a QIAquick affinity column and dephosphorylated for 1 h at 37° C. in the presence of 12 μl of 10×buffer 3 (New England Biolabs) and 5000 units of calf intestine alkaline phosphatase (CIP, New England Biolabs), and finally purified once again on a QIAquick affinity column.

The fragment SpeI/DraIII of 70 bp containing the two as-2 elements and the as-1 element was obtained from the plasmid pMRT1111. This latter plasmid, which contains a 58 bp sequence corresponding to a duplication of the as-2 element (Lam et Chua, 1989) and an as-1 element (Lam et al., 1989) originating from the 35S RNA CaMV promoter upstream of the minimal pea plastocyanin promoter modified by the addition of a "G" box, was obtained by 1b-PCR in the following manner. The single stranded continuous DNA was generated using the following "directional" desoxynucleotides:

```
- S1 =
5' TTCCCTTCAAACACATACAAATTCAGTAGAGAAGAAACTCATTACTCTTGAGAAACCTAGAGGATCCCCG 3'    (SEQ ID NO: 34)

- S2 =
5' CACAAAAACCCAATCCACATCTTTATCATCCATTCTATAAAAAATCACCTTCTGTGTGTCTCTCTTTCGA 3'    (SEQ ID NO: 35)

- S5 =
```

-continued

```
S' CTGTGGCACATCTACATTATCTAAATCTAAGCCACGTCGGAGGATAACATATTCTTCCACACATCTTAGCCA 3'                (SEQ ID NO: 36)

- S7 =
5' CATGCTGCAGACTAGTGATTGATGTGATATCAAGATTGATGTGATATCTCCACTGACGTAAGGGATGACGCATGCCACT 3'        (SEQ ID NO: 14)
```

One hundred picomoles (100 pmol) of the desoxynucleotides S1, S2 and S5 were 5' phosphorylated with 15 units of kinase (Amersham) in the presence of 5 µl 10×kinase buffer (Amersham) and 500 pmol of ATP (Sigma), for 30 min at 37° C. The phosphorylated oligodesoxynucleotides were purified by extraction with a volume of phenol, then a volume of phenol:chloroform:isoamyl alcohol (25:24:1 v/v/v) and finally a volume of chloroform:isoamyl alcohol (24:1 v/v), before being precipitated with ⅒ volume 3M sodium acetate pH 4.8 and 2.5 volumes absolute ethanol at −80° C. for 20 min then centrifuged at 16060 g for 30 min. The precipitated oligodesoxynucleotides were washed in 70% ethanol, dried, then resuspended in water at a concentration of 10 pmol/µl. In order to link the "directional" oligodesoxynucleotides, the following "guide" oligodesoxynucleotides were used:

```
- G1 = 5' TGTGTTTGAAGGGAATCGAAAGAGAGACACA 3'    (SEQ ID NO: 37)

- G2 = 5' GATTGGGTTTTTGTGTGGCTAAGATGTGTG 3'     (SEQ ID NO: 38)

- G4 = 5' TGTAGATGTGCCACAGAGTGGCATGCGT 3'       (SEQ ID NO: 39)
```

In order to carry out the LCR reaction, 10 pmol of the phosphorylated directional desoxynucleotides S1, S2, S5 and S7 were ligated in the presence of 10 pmol of the "guide" desoxynucleotides G1, G2 and G4, 5 µl Taq 10×DNA ligase buffer (New England Biolabs) and 40 units Taq DNA ligase (New England Biolabs). The ligation reaction was carried out in a GeneAmp PCR System 9700 thermocycle (Perkin Elmer, Norwalk, USA). It consists of a cycle of 1 min at 94° C., and 8 identical cycles each consisting of the succession of the following steps: 1 min at 65° C., 1 min at 57° C., 1 min at 52° C., 1 min at 48° C., 1 min at 43° C., and finally 10 min at 37° C. Then, the ligation reaction mixture was purified on a QIAquick affinity column according to the supplier's recommendations.

Finally, PCR amplification of the single stranded continuous DNA obtained was carried out in a GeneAmp PCR System 9700 thermocycle in the presence of 100 pmol of each of the following oligodesoxynucleotide probes 5' CATGCTGCAGACTAGTGGATT 3', (SEQ ID NO: 29), and 5' CGGGGATCCTCTAGGTTTCT 3' (SEQ ID NO: 30), 50 nmol of each of the dNTP, 10 µl of Vent 10×DNA polymerase buffer (New England Biolabs), and 2 units of Vent DNA polymerase (New England Biolabs). The DNA was denatured for 5 min at 94° C., subjected to 25 cycles each consisting of a 30 sec denaturing step at 95° C., a 30 sec hybridisation step at 56° C., and a 1 min elongation step at 72° C., then further elongation at 72° C. for 5 min.

The DNA fragments of the reaction mixture were digested for 45 min at 37° C. with 20 units of BamHI, then for 1 h at 37° C. with 20 units of PstI, and finally purified on a QIAquick column. They were inserted into the plasmid pGEM3Z-petE prom digested for 1 h at 37° C. with BamHI, then for 1 h at 37° C. with PstI, subjected to 0.8% agarose gel electrophoresis, purified on a QIAquick affinity column, dephosphorylated for 1 h at 37° C. in the presence of 12 µl of 10×buffer 3 (New England Biolabs) and 5000 units of calf intestine alkaline phosphatase (CIP, New England Biolabs), and finally purified on a QIAquick affinity column. In order to carry out the ligation, 25 ng of plasmid treated as described above were contacted with 100 ng of the DNA fragments obtained by PCR, in the presence of 1,2 µl of T4 10×DNA ligase buffer (New England Biolabs) and 400 units T4 DNA ligase (New England Biolabs) for 1 night at 18° C. Previously prepared viable and competent *Escherichia coli* DH5α bacteria were transformed with half of the ligation reaction mixture. The DNA of the obtained clones, selected on LB media supplemented with ampicillin (50 mg/l), was extracted according to the alkaline lysis method and was analysed by enzymatic digestion. The promoter sequence MPr1111 of one of these clones was verified by sequencing.

The 70 bp fragment containing the two as-2 elements and the as-1 element was obtained by digesting 25 µg of plasmid pMRT1111 with 40 units of SpeI for 1 h at 37° C., then with 4 units of DraIII for 1 h at 37° C. The fragment was isolated by electrophoresis on Nu-Sieve 3% gel agarose (FMC, Rockland, USA) and finally purified on a QIAquick affinity column.

The ligation was carried out with 30 ng of dephosphorylated plasmid vector pMRT1116 NheI/DraIII and 50 ng of the 70 bp fragment for 15 h at 18° C. in a reaction volume of 20 µl in the presence of 2.0 µl T4 10×DNA ligase buffer (New England Biolabs) and 800 units T4 DNA ligase (New England Biolabs). Previously prepared viable and competent *Escherichia coli* DH5α bacteria were transformed with half of the ligation reaction mixture. The plasmid DNA of the obtained clones, selected on LB media supplemented with ampicillin (50 mg/l), was extracted according to alkaline lysis method, and analysed by enzymatic digestion and gene amplification using the desoxynucleotides 5' CATGCTGCAGACTAGTATCC 3' (SEQ ID NO:26) selected on the promoter and 5' TTGATTTCACGGGTTGGG 3' (SEQ ID NO:28) selected on the uidA sequence. The promoter sequence MPr1146 (SEQ.ID05) of one of these clones was verified by sequencing.

2.3. Construction of the Promoter MPr1147:

The promoter MPr1147 (FIG. IV) was obtained by inserting a sequence of 44 bp from the RNA 35S CaMV promoter containing the elements as-2 and as-1 (Lam, 1989; Lam et al., 1989) and restriction sites adjacent to sites NheI and DraIII of MPr1117 (SEQ.ID04).

In order to achieve this, the plasmid pMRT1117 was digested with 25 units of NheI for 1 h at 37° C. then purified on a QIAquick affinity column. The ends generated were blunted by the action of Pfu DNA polymerase (Stratagene, La Jolla, USA) according to the supplier's recommendations, then the plasmid obtained was digested for 1 h at 37° C. with 4 units of DraIII. The thus modified plasmid was isolated on 0.8% agarose gel, purified on a QIAquick affinity column and dephosphorylated for 1 h at 37° C. in the presence of 12 µl of 10×buffer 3 (New England Biolabs) and 5000 units of calf intestine alkaline phosphatase (CIP, New England Biolabs), and finally purified again on a QIAquick affinity column.

The 54 bp fragment PstI/DraIII containing the 44 bp of the as-2 and as-1 elements of the CaMV 35S was obtained from plasmid pMRT1110. The plasmid pMRT1110, which contains a sequence of 44 bp corresponding to the as-2 element (Lam et Chua, 1989) and the as-1 element (Lam et al., 1989) of the 35S RNA CaMV promoter upstream of the minimal pea plastocyanine promoter modified by the addition of a "G" box, was obtained by lb-PCR in the following manner. The single stranded continuous DNA was formed using the "guide" desoxynucleotides:

- S1 = 5' TTCCCTTCAAACACATACAAATTCAGTAGAGAAGAAACTCATTACTCTTGAGAAACCTAGAGGATCCCCG 3' (SEQ ID NO: 34)
- S2 = 5' CACAAAAACCCAATCCACATCTTTATCATCCATTCTATAAAAAATCACCTTCTGTGTGTCTCTCTTTCGA 3' (SEQ ID NO: 35)
- S5 = 5' CTGTGGCACATCTACATTATCTAAATCTAAGCCACGTCGGAGGATAACATATTCTTCCACACATCTTAGCCA 3' (SEQ ID NO: 36)
- S6 = 5' CATGCTGCAGACTAGTGGATTGATGTGATATCTCCACTGACGTAAGGGATGACGCATGCCACT 3' (SEQ ID NO: 13)

One hundred picomoles (100 pmol) of the desoxynucleotides S1, S2 and S5 were phosphorylated in 5' by 15 units of kinase (Amersham) in the presence of 5 µl 10×kinase buffer (Amersham) and 500 pmol ATP (Sigma), for 30 min at 37° C. The phosphorylated oligodesoxynucleotides were purified by extraction extraction with a volume of phenol, then a volume of phenol:chloroform:isoamyl alcohol (25:24:1 v/v/v) and finally a volume of chloroform:isoamyl alcohol (24:1 v/v), before being precipitated with 1/10 volume 3M sodium acetate pH 4.8 et 2.5 volumes absolute ethanol at −80° C. for 20 min then centrifuged at 16060 g for 30 min. The precipitated oligodesoxynucleotides were washed in 70% ethanol, dried, then resuspended in water at a concentration of 10 pmol/µl. In order to link the "directional" oligodesoxynucleotides, the following "guide" oligodesoxynucleotides were used:

- G1 = 5'
TGTGTTTGAAGGGAATCGAAAGAGAGACACA 3' (SEQ ID NO: 37)

- G2 = 5'
GATTGGGTTTTTGTGTGGCTAAGATGTGTG 3' (SEQ ID NO: 38)

- G4 = 5'
TGTAGATGTGCCACAGAGTGGCATGCGT 3' (SEQ ID NO: 39)

In order to carry out the LCR reaction, 10 pmol of the phosphorylated "directional" desoxynucleotides S1, S2, S5 and S6 were ligated in the presence of 10 pmol of the "guide" desoxynucleotides G1, G2 and G4, 5 µl Taq 10×DNA ligase buffer and 40 units Taq DNA ligase (New England Biolabs). The ligation reaction was carried out in a GeneAmp PCR System 9700 thermocycle.

It consists of a cycle of 1 min at 94° C., and 8 identical cycles each consisting of the succession of the following steps: 1 min at 65° C., 1 min at 57° C., 1 min at 52° C., 1 min at 48° C., 1 min at 43° C., and finally 10 min at 37° C. Then, the ligation reaction mixture was purified on a QIAquick column according to the supplier's recommendations.

Finally, PCR amplification of the single stranded DNA obtained was carried out in a thermocycleur GeneAmp PCS System 9700 in the presence of 100 pmol of each of the oligodesoxynucleotide probes 5' CATGCTGCAGAC-TAGTGGATT 3' (SEQ ID NO:29), and 5' CGGGGATC-CTCTAGGTTTCT 3' (SEQ ID NO:30), of 50 nmol of each of the dNTP, of 10 µl of 10×Vent DNA polymerase buffer (New England Biolabs), and 2 units Vent DNA polymerase (New England Biolabs). The DNA was denatured for 5 min at 94° C., subjected to 25 cycles each consisting of a 30 sec denaturing step at 95° C., a 30 sec hybridisation step at 56° C., and of 1 min elongation at 72° C., then further elongation at 72° C. for 5 min. The DNA fragments of the reaction mixture were digested for 45 min at 37° C. with 20 units of BamHI then for 1 h at 37° C. with 20 units of PstI, and finally purified on a QIAquick column. They were inserted in the plasmid pGEM3Z-petE prom digested for 1 h at 37° C. with BamHI then for 1 h at 37° C. with PstI, subjected to 0.8% agarose gel electrophoresis, purified on a QIAquick affinity column, dephosphorylated for 1 h at 37° C. in the presence of 12 µl of 10×buffer 3 (New England Biolabs) and 5000 units of calf intestine alkaline phosphatase (CIP, New England Biolabs), and finally purified on a QIAquick affinity column. To carry out the ligation, 25 ng of plasmid treated as described above were contacted with 100 ng of the DNA fragments obtained by PCR,in the presence of 1.2 µl of T4 10×DNA ligase buffer (New England Biolabs) and 400 units T4 DNA ligase (New England Biolabs) for 1 night at 18° C. Previously prepared viable and competent *Escherichia coli* DH5α bacteria were transformed with half of the ligation reaction mixture. The DNA of the obtained clones, selected on LB media supplemented with ampicillin (50 mg/l), was extracted according to alkaline lysis method and analysed by enzymatic digestion. The promoter sequence MPr1110 borne by this plasmid pMRT1110 was verified by sequencing.

The 54 bp fragment containing the sequences as-2 and as-1 originating from the CaMV promoter was obtained by digesting 25 µg of the plasmid pMRT1110 for 1 h at 37° C. with 80 units of PstI, then the generated ends were blunted by the action of Pfu DNA polymerase (Stratagene, La Jolla, USA) according to the supplier's recommendations. The plasmid thus modified was digested for 1 h at 37° C. with 4 units of DraIII, and the 54 bp fragment was isolated by electrophoresis on 3% Nu-Sieve agarose gel (FMC, Rockland, USA) and finally purified on a QIAquick affinity column. The ligation was carried out with 30 ng of-vector pMRT1117 prepared as described previously and 50 ng of the 54 bp fragment for 15 h at 18° C. in a reaction volume of 20 µl in the presence of 2.0 µl of T4 10×DNA ligase buffer (New England Biolabs) and 800 units T4 DNA ligase (New England Biolabs). Previously prepared viable and competent *Escherichia coli* DH5α bacteria were transformed with half of the ligation reaction mixture. The plasmid DNA of the obtained clones, selected on LB media supplemented with ampicillin (50 mg/l), was extracted according to the alkaline lysis method, and analysed by enzymatic digestion and gene amplification using the desoxynucleotides 5' CATGCTG-CAGACTAGTATCC 3' (SEQ ID NO 26) selected from the promoter and 5' TTGATTTCACGGGTTGGG 3' (SEQ ID NO 28) selected from the uidA sequence. The promoter sequence MPr1147 (SEQ.ID06) of one of these clones was verified by sequencing.

2.4. Construction of the Promoter MPr1154:

The promoter MPr1154 (FIG. IV) was obtained by deleting a 44 bp sequence containing the duplicated as-1-like element from CoYMV present in the promoter MPr1147 (SEQ.ID04).

In order to achieve this, the plasmid pMRT1147 was digested with 20 units of SpeI for 1 h at 37° C., isolated on 0.8% gel agarose, purified on a QIAquick affinity column and religated for 15 h at 18° C. in a reaction volume of 10 µl in the presence of 1 µl of T4 10×DNA ligase buffer (New England Biolabs) and 400 units T4 DNA ligase (New England Biolabs). Previously prepared viable and competent *Escherichia coli* DH5α bacteria were transformed with half of the ligation reaction mixture. The plasmid DNA of the obtained clones, selected on LB media supplemented with ampicillin (50 mg/l), was extracted according to the alkaline lysis method, and analysed by enzymatic digestion and gene amplification using the desoxynucleotides 5' ATTTAGGT-GACACTATAG 3' (SEQ ID NO:31) selected from the plasmid and 5' TTGATTTCACGGGTTGGG 3' (SEQ ID NO:28) selected from the uidA sequence. The promoter sequence MPr1154 (SEQ.ID07) of one of these clones was verified by sequencing.

2.5. Construction of the Promoters MPr1162, MPr1163, MPr1164, MPr1165:

The promoters MPr1162, MPr1163, MPr1164, and MPr1165 (FIG. VII) were obtained by inserting one or multiple copies of the 70 bp sequence corresponding to a duplication of the as-2 box (Lam and Chua, 1989) and the as-1 box (Lam et al., 1989) of the 35S RNA CaMV promoter, bearing restriction sites on either side, into the site BstEII from MPr1116 (SEQ.ID03), in the 5'>3' orientation or inverted, that is to say, in the 3'>5' orientation.

In order to do this, the plasmid pMRT1116 was digested with 4 units of BstEII for 1 h at 37° C. then purified on a QIAquick affinity column. The generated ends were blunted by the action of Pfu DNA polymerase (Stratagene, La Jolla, USA) according to the recommendations of the supplier, then dephosphorylated for 1 h at 37° C. in the presence of 12 µl of 10×"buffer 3" (New England Biolabs) and 25 units of calf intestine alkaline phosphatase (CIP, New England Biolabs). Finally, the thus obtained plasmid was purified again on a QIAquick affinity column.

The 70 bp SpeI/DraIII fragment containing the two "as-2" boxes and the "as-1" box was obtained from plasmid pMRT1111.

The plasmid pMRT1111, which contains a 58 bp sequence corresponding to a duplication of the as-2 box (Lam et Chua, 1989) and the as-1 box (Lam et al., 1989) from the 35S RNA CaMV promoter placed upstream of the minimal pea plastocyanine promoter modified by the addition of a "G" box, was obtained by lb-PCR in the following way. The single stranded DNA was produced with the help of the following directional oligodesoxynucleotides:

One hundred picomoles (100 pmol) of the S1, S2 et S5 oligodesoxynucleotides were 5' phosphorylated with 15 units of kinase (Amersham) in the presence of 5 µl 10×kinase buffer (Amersham) and 500 pmol ATP (Sigma), for 30 min at 37° C. The phosphorylated desoxynucleotides were purified by extraction with a volume of phenol, then a volume of phenol:chloroform:isoamyl alcohol (25:24:1 v/v/v) and finally a volume of chloroform:isoamyl alcohol (24:1 v/v), before being precipitated by ¹⁄₁₀ volume 3M sodium acetate pH 4.8 and 2.5 volumes absolute ethanol at −80° C. for 20 min then centrifuged at 16060 g for 30 min. The precipitated oligodesoxynucleotides were washed in 70% ethanol, dried, then resuspended in water at a concentration of 10 pmol/ml. In order to link the directional oligodesoxynucleotides, the following guide oligodesoxynucleotides were used:

```
- G1 = 5'
TGTGTTTGAAGGGAATCGAAAGAGAGACACA 3'   (SEQ ID NO: 37)

- G2 = 5'
GATTGGGTTTTTGTGTGGCTAAGATGTGTG 3'    (SEQ ID NO: 38)

- G4 = 5'
TGTAGATGTGCCACAGAGTGGCATGCGT 3'      (SEQ ID NO: 39)
```

In order to carry out the LCR reaction, 10 pmol of the phosphorylated oligodesoxynucleotides S1, S2, S5 and S7 were ligated in the presence of 10 pmol of the guide oligodesoxynucleotides G1, G2 and G4, 5 µl of Taq 10×DNA ligase buffer (New England Biolabs) and 40 units Taq DNA ligase (New England Biolabs). The ligation reaction was carried out in a thermocycle, sold under the tradename GENEAMP PCR System 9700 (Perkin Elmer, Norwalk, USA). It consisted of a cycle of 1 min at 94° C., and 8 identical cycles each consisting of the succession of the following steps: 1 min at 65° C., 1 min at 57° C., 1 min at 52° C., 1 min at 48° C., 1 min at 43° C., and finally 10 min at 37° C. Then, the ligation reaction mixture was purified on a QIAquick column according to the suppliers's recommendations.

Finally, PCR amplification of the the single stranded DNA obtained was carried out in a "GeneAmp PCR System 9700" thermocycle in the presence of 100 pmol of each of the oligodesoxynucleotide probes 5' CATGCTGCAGAC-TAGTGGATT 3'(SEQ ID NO:29), and 5' CGGGGATC-CTCTAGGTTTCT 3', 50 (SEQ ID NO:30), 50 nmol of each dNTP, 10 µl of Vent 10×DNA polymerase buffer (New England Biolabs), and 2 units Vent DNA polymerase (New England Biolabs). The DNA was denatured for 5 min at 94° C., subjected to 25 cycles each consisting of a 30 sec denaturing step at 95° C., of a 30 sec hybridisation step at 56° C., and of 1 min elongation at 72° C., then further elongation at 72° C. for 5 min.

The DNA fragments from the reaction mixture were digested for 45 min at 37° C. by 20 units of BamHI, then for

```
- S1 =
5' TTCCCTTCAAACACATACAAATTCAGTAGAGAAGAAACTCATTACTCTTGAGAAACCTAGAGGATCCCCG 3'        (SEQ ID NO: 34)

- S2 =
5' CACAAAAACCCAATCCACATCTTTATCATCCATTCTATAAAAAATCACCTTCTGTGTGTCTCTCTTTCGA 3'        (SEQ ID NO: 35)

- S5 =
5' CTGTGGCACATCTACATTATCTAAATCTAAGCCACGTCGGAGGATAACATATTCTTCCACACATCTTAGCCA 3'      (SEQ ID NO: 36)

- S7 =
5' CATGCTGCAGACTAGTGATTGATGTGATATCAAGATTGATGTGATATCTCCACTGACGTAAGGGATGACGCATGCCACT 3'   (SEQ ID NO: 14)
```

1 h at 37° C. by 20 units of PstI, and finally purified on a QIAquick column. They were inserted into the plasmid pGEM3Z-petE prom previously digested for 1 h at 37° C. by BamHI, then for 1 h at 37° C. by PstI, subjected to electrophoresis on 0.8% agarose gel, purified on a QIAquick affinity column, dephosphorylated for 1 h at 37° C. in the presence of 12 µl of 10×"buffer 3" (New England Biolabs) and 25 units of calf intestine alkaline phosphatase (CIP, New England Biolabs), and finally purified on a QIAquick affinity column. In order to carry out ligation, 25 ng of the thus treated plasmid was contacted with 100 ng of the DNA fragments obtained by PCR, in the presence of 1.2 µl of T4 10×DNA ligase buffer (New England Biolabs) and 400 units of T4 DNA ligase (New England Biolabs) for 1 night at 18° C. Previously prepared viable and competent *Escherichia coli* DH5α bacteria were transformed half of the ligation reaction mixture. The DNA of the obtained clones, selected on LB media supplemented with ampicillin (50 mg/l), was extracted according to the alkaline lysis method and analysed y enzymatic digestion. The promoter sequence MPr1111 of one of the obtained clones was verified by sequencing.

The 70 bp fragment containing the two "as-2" boxes and the "as-1" box were obtained by digestin 25 mg of plasmid pMRT1111 with 40 units of SpeI for 1 h at 37° C., then with 4 units of DraIII for 1 h at 37° C. The fragment was isolated by electrophoresis on a 3% agarose gel sold under the tradename NU SIEVE (FMC, Rockland, USA) and finally purified on a QIAquick affinity column. The ends of this fragment were blunted by the action of Pfu DNA polymerase (Stratagene, La Jolla, USA) according to the recommendations of the supplier, then purified again on a QIAquick affinity column.

The ligation was carried out with 30 ng of pMRT1116 vector prepared as described above and 50 ng of 70 bp fragment for 15 h at 18° C. in a reaction mixture of 20 µl in the presence of 20 µl of 10×T4 DNA ligase buffer (New England Biolabs) and 400 units of T4 DNA ligase (New England Biolabs). Previously prepared viable and competent *Escherichia coli* DH5α bacteria, were transformed with a third of the ligation reaction mixture. The plasmid DNA of the obtained clones, selected on LB media supplemented with ampicillin (50 mg/l), was extracted according to the alkaline lysis method, and analysed by enzymatic digestion and by gene amplification with the help of the universal SP6 oligodesoxynucleotide (5' TAAATCCACTGTGATATCT-TATG 3') (SEQ ID NO:32) located in the 5' region of the promoter and the oligodesoxynucleotide 5' TTGATTTCACGGGTTGGG 3' (SEQ ID NO:28) selected on the uidA sequence. This cloning strategy enabled the production of 70 bp fragment inserts into the vector in the 5'>3' orientation (the sequences as-2/as-2/as-1 are cloned in the same orientation as in their native promoter), in 3'>5' antisens orientation (an orientation inverse to that present in the CaMV 35S promoter) and in one or more copies. The following synthetic and chimeric promoters could be obtained Using this strategy: MPr1162 (SEQ.ID19), which corresponds to the insertion of a single 70 bp sequence in normal 5'>3' orientation, MPr1163 (SEQ.ID20), which corresponds to the insertion of two 70 bp sequences in the normal 5'>3' orientation, MPr1164 (SEQ.ID21), which corresponds to the insertion of a single 70 bp sequence in inverse or antisens orientation, and MPr1165 (SEQ.ID22), which corresponds to the insertion of four 70 bp sequences in normal 5'>3' orientation. Each one of these clones was verified by sequencing.

2.6. Construction of Promoters MPr1167, MPr1168, and MPr1169

The promoters MPr1167, MPr1168 and MPr1169 (FIG. VII) are derived from MPr1147 (SEQ.ID06). They were obtained by inserting, into the BstEII site of MPr1147, one or more normally 5'>3' oriented (i.e. cloned in the same orientation as the native orientation of the sequences in the CaMV promoter) 70 bp sequences containing the 58 bp sequence corresponding to a duplication of the as-2 box (Lam et Chua, 1989) and the as-1 box (Lam et al., 1989) of the 35S RNA CaMV promoter.

In order to do this, the plasmid pMRT1147 was digested with 4 units of BstEII for 1 h at 37° C. then purified on a QIAquick affinity column. The generated ends were blunted by the action of Pfu DNA polymerase (Stratagene, La Jolla, USA) according to the recommendations of the supplier, then dephosphorylated for 1 h at 37° C. in the presence of 12 µl of 10×"buffer 3" (New England Biolabs) and 25 units of calf instestine alkaline phosphatase (CIP, New England Biolabs). Finally the plasmid thus obtained was purified again on a QIAquick affinity column.

The 70 bp SpeI/DraIII fragment containing the two "as-2" boxes and the "as-1" box was obtained from plasmid pMRT1111, the production of which was described previously. The ends of this fragment were blunted as described above.

The ligation was carried out with 30 ng of vector pMRT1147 prepared as described previously and 50 ng of the 70 bp fragment for 15 h at 18° C. in a reaction mixture of 20 µl in the presence of 2.0 µl 10×T4 DNA ligase buffer (New England Biolabs) and 400 units T4 DNA ligase (New England Biolabs). Previously prepared viable and competent *Escherichia coli* DH5α transformed by reacting with a third of the ligation reaction mixture. The plasmid DNA of the obtained clones, selected on LB media supplemented with ampicillin (50 mg/l), was extracted according to the alkaline lysis method, and analysed by enzymatic digestion and by gene amplification using the universal SP6 oligodesoxynucleotide (51' TAAATCCACTGTGATATCTTATG 3'(SEQ ID NO:32)) located in the 5' region of the promoter and the oligodesoxynucleotide 5' TTGATTTCACGGGTTGGG 3' (SEQ ID NO:28) selected from the uidA sequence. The following synthetic promoters could be prepared by the preceding method: MPr1167 (SEQ.ID23), which corresponds to the insertion of three 70 bp sequences in normal 5'>3' orientation, MPr1168 (SEQ.ID24), which corresponds to the insertion of two 70 bp sequences in normal 5'>3' orientation and MPr1169 (SEQ.ID25), which corresponds to the insertion of a single 70 bp sequence in normal 5'>3' orientation. Each of these clones was verified by sequencing.

2.7. Production of Binary Vector pMRT1218 Containing Promoter MPr1218:

The reference promoter for expression of the GUS reporter gene in corn seed endosperm is the promoter of gene coding for a storage protein in corn seed of 28 kDa belonging to the family of gamma-zeins. This construct has been described in French patent application number FR9912373, filed on Sep. 30th, 1999, in the name of the applicants, and is incorporated herein for the purposes of the specific description of said reference promoter and vector. The 1.7 kb γ-zein whole length promoter sequence (Prγ-zein) contained in the plasmid p63 described by Reina et al. (1990) was placed upstream of the uidA-IV2/term-nos sequence in a vector designated pMRT1126. The vector pMRT1126 is described in full in the abovementioned French patent application, and its description is incorporated herein for the purposes of the description of this vector. The promoter Mpr1126 in vector pMRT1126 derives from the HMWG-Dx5 (High Molecular Weight Glutenin) promoter by deletion of the sequence situated upstream of nucleotide −142, which sequence comprises two "prolamine like" boxes, two "GATA" boxes, a "G" box and and an activator element. The promoter fragment was amplified by PCR and isolated.

The 1.7 kb γ-zein promoter was obtained by digesting 15 μg of plasmid p63 with restriction enzymes HindIII and BamHI for 1 h at 37° C. The thus liberated 1.7 kb Prγ-zein fragment was isolated on 0.8% agarose gel using a gel kit under the tradename CONCERT Rapid Gel Extraction System.

In parallel, 10 μg of plasmid pMRT1126 were digested by the restriction enzymes HindIII and BamHI for 1 h at 37° C. The vector fragment was then isolated on 0.8% agarose gel using a <<Concert Rapid Gel Extraction System >> kit and dephosphorylated with 40 units of calf intestine alkaline phosphatase (New England Biolabs) in the presence of 10x"buffer 3" at 37° C. for 1 h.

The ligation reaction was carried out with 50 ng of γ-zein promoter fragment and 100 ng of plasmid pMRT1126, in a reaction volume of 10 μl, in the presence of tampon T4 10×DNA ligase and 400 units of T4 DNA ligase (New England Biolabs), in a thermocyle sold under the trade name GENEAMP PCR System 9700 as described above. Previously prepared viable and competent *Escherichia coli* DH5α bacteria were transformed with all of the ligation reaction mixture. The plasmid DNA of the obtained clones, selected on LB media supplemented with ampicillin (50 mg/l), was extracted according to the alkaline lysis method and analysed by enzymatic digestion. The resulting plasmid was designated pMRT1218.

3. Construction of Binary Plasmids Containing the Promoters.

Three types of binary vector were used for cloning the various expression cassettes. The vector pGA492 was used to prepare the cassettes containing MPr1116, MPr1146, MPr1147 and MPr1092 to create the expression cassettes or binary vectors pMRT1152, pMRT1171, pMRT1172 and pGA492MPr1092 respectively. The vector pGA492 was prepared as follows. A 25 μg amount of plasmid pGA492 (An, 1986) was digested with 80 units of HindIII for 1 h at 37° C. then purified on a QIAquick affinity column. The 5' protruding ends of this plasmid were blunted using Pfu DNA polymerase (Stratagene, La Jolla, USA) according to the supplier's recommendations. The thus modified plasmid was digested with 80 units of EcoRI for 1 h at 37° C., then the vector deleted of its 291 bp fragment was isolated on 0.7% agarose gel and purified on a QIAquick affinity column. A 25 μg amount of plasmid pGA492 (An, 1986) was digested with 80 units of HindIII for 1 h at 37° C. then purified on a QIAquick affinity column.

The vector pMRT1118 was used to clone the cassettes under control of the promoters MPr1162, MPr1164, MPr1165, MPr1167 and MPr1092 to give the vectors pMRT1185, pMRT1186, pMRT1187, pMRT1188 and pMRT1182 respectively.

The plasmid pMRT1118 is described completely in French patent application number FR9911112, filed on Sep. 3, 1999, also in the name of the present applicant, the specific description of which is incorporated herein by reference. The binary plasmid pMRT1118 (5971 pb) results from the introduction of a T-DNA fragment digested by AvrII enzyme into the AvrII site of another dephosphorylated plasmid also fully described in the previously mentioned prior application to same applicant, and designated pMRT1106, also specifically incorporated herein by reference.

In order to carry out the insertion, the pMRT1106 plasmid DNA (5 μg) was digested with AvrII enzyme, purified with the aid of a PCR purification kit sold under the tradename QIAQUICK, then dephosphorylated with 50 units of calf intestine alkaline phosphatase (New England Biolabs) in a final reaction mixture volume of 120 μl in the presence of 12 μl 3×10 buffer (New England Biolabs) at 37° C. for 1 hour, isolated by electrophoresis on at 0.6% agarose gel in TBE buffer, purified with a gel extraction kit sold under the tradename QIAQUICK, dephosphorylated a second time with the calf intestine alkaline phosphatase under the conditions mentioned above, and finally purified with a a PCR purification kit sold under the tradename QIAQUICK and transferred to 50 μl de $H_2O$.

The PCR ligation reaction was carried out with 32,5 g of digested dephosphorylated plasmid pMRT1106 and 50 ng of T-DNA fragments digested in a reaction mixture volume of 10 μl in the presence of 1 μl T4 10×DNA ligase buffer (New England Biolabs) and 400 units of T4 DNA ligase (New England Biolabs). The ligation comprised 180 cycles each including 2 steps, the first one at 10° C. for 30 seconds and the second step at 30° C. for 30 seconds in a thermocycle sold under the tradename GENEAMP PCR System 9700.

Previously prepared viable and competent *Escherichia coli* DH5α bacteria, were transformed (Hanahan, 1983). The plasmid DNA of the obtained clones, selected on LB media supplemented with kanamycin (50 mg/l), was extracted according to the alkaline lysis method (Birnboim et Doly, 1979) and verified by enzymatic digestion and sequencing. The resulting plasmid was designated pMRT1118.

This vector was then prepared in the following manner: a 25 μg amount of plasmid was digested with 80 units of HindIII for 1 h at 37° C. then purified on a QIAquick affinity column. The 5' protruding ends of this plasmid were blunted using Pfu DNA polymerase (Stratagene, La Jolla, USA) according to the supplier's recommendations. The thus modified plasmid was digested with 80 units of EcoRI for 1 h at 37° C., then the vector was isolated on 0.7% agaros gel and purified on a QIAquick affinity column. This was then dephosphorylated for 1 h at 37° C. using 10 units of calf intestine alkaline phosphatase (New England Biolabs) according to the manufacturer's recommendations, then purified on a QIAquick affinity column.

The vector pMRT1195 was used to clone the cassettes under the control of the promoters MPr1116, MPr1154, MPr1162, MPr1163, MPr1164, MPr1165, MPr1167, MPr1168, MPr1169 and MPr1092 to give the vectors pMRT1245, pMRT1246, pMRT1247, pMRT1248, pMRT1249, pMRT1250, pMRT1251, pMRT1252, pMRT1253 and pMRT1254 respectively. The vector pMRT1195, which is also described in the prior French application number FR 9911112, filed on Sep. 3, 1999, also in the name of the present applicant, and incorporated herein by reference to that particular aspect, comprises in order: an ori RK2 region followed by an ori ColEI region, followed by nptIII and an nptII regions and then a trfA region, subsequently followed by a transfer DNA left border region, a nos terminator region, a bar region (coding for phosphinotricine acetyl transferase, a protein conferring herbicide resistance), a rice actin intron-1 region, a polyadenylation transcription termination signal region, a multiple cloning site region and then a transfer DNA right border region. The vector pMRT1195 was prepared in the following manner.

A 20 μg amount of plasmid pMRT1195 was digested by 15 units of HpaI for 1 h at 37° C. then purified on a QIAquick affinity column. The thus opened vector was dephosphorylated for 1 h at 37° C. using 10 units of calf intestine alkaline phosphatase (New England Biolabs) according to the manufacturer's recommendations, then purified on a QIAquick affinity column.

3.1 Production of pMRT1152.

The expression cassette MPr1116/uidA-IV2/nos term was cloned at the modified HindIII site of the binary plasmid pGA492. It was obtained from the plasmid pMRT1116 digested with 80 units of PstI for 1 h at 37° C. and purified on an affinity column sold under the tradename QIAQUICK. The protruding 5' ends of this plasmid were blunted using Pfu DNA polymerase (Stratagene, La Jolla, USA) according to the supplier's recommendations. The plasmid thus modified was digested simultaneously with 80 units of EcoRI and 40 units of XmnI for 1 h at 37° C., then the 2.5 kb DNA fragment corresponding to the expression cassette was separated on 1% agarose gel and purified on an affinity column sold under the tradename QIAQUICK.

The ligation was carried out by mixing 100 ng of binary plasmid pGA492 prepared as described above and 50 ng of expression cassette for 1 night at 18° C. in a reaction volume of 20 µl in the presence of 2 µl of T4 10×DNA ligase buffer (New England Biolabs) and 400 units of T4 DNA ligase (New England Biolabs). Previously prepared viable and competent *Escherichia coli* DH5α bacteria were transformed with half of the ligation reaction mixture. The plasmid DNA of the obtained clones, selected on LB media supplemented with tetracycline (12 mg/l), was extracted according to the alkaline lysis method and analysed by enzymatic digestion as well as by gene amplification using the desoxynucleotides 5' ATATGAGACTCTAATTG-GATACCGAGGGG 3' (SEQ ID NO:33) selected from the transfer DNA of the binary plasmid and 5' TTGATTTCACGGGTTGGG 3' (SEQ ID NO28) selected from the the expression cassette in the uidA sequence. The resulting clone was designated pMRT1152.

3.2. Production of the Binary Plasmid pMRT1171.

The expression cassette MPr1146/uidA-IV2/nos term was cloned at the modified HindIII site of the binary plasmid pGA492 by following the same protocol as for plasmid pMRT1152, except that the expression cassette was isolated from the plasmid pMRT1146. The resulting clone was designated pMRT1171.

3.3. Production of the Binary Plasmid pMRT1172.

The expression cassette MPr1147/uidA-IV2/nos term was cloned at the modified HindIII site of the binary plasmid pGA492 by following the same protocol as for the plasmid pMRT1152, except that the expression cassette was isolated from the plasmid pMRT1147. The resulting clone was designated pMRT1172.

3.4. Production of the Binary Plasmid pGA492MPr1092.

The promoter fragments MPr1092 and uidA-IV2/nos term sequence were inserted into the binary plasmid pGA492 prepared as described above. The two fragments were prepared in the following manner:

CaMV D35S prom was isolated by digesting 10 µg of plasmid pJIT163Δ with 40 units of KpnI for 1 h at 37° C. The ends of this linearized plasmid were blunted using 6 units of T4 DNA polymerase (New England Biolabs) for 30 min at 37° C. according to the manufacturer's recommendations. The plasmid thus modified was purified on a QIAquick affinity column, then redigested with 80 units of HindIII for 1 h at 37° C. The 743 bp fragment corresponding to the promoter was separated on 0.8% agarose gel, then purified on a QIAquick affinity column.

the cassette "uidA-IV2/nos term" was obtained by digesting 4 µg of the plasmid pMRT1092 with 40 units of HindIII and EcoRI for 1 h. The 2.2 kb fragment corresponding to the sequence uidA-IV2/nos term was separated on 0.8% agarose gel, then purified on a QIAquick affinity column.

The ligation between the three fragments was carried out by mixing 100 ng of binary plasmid, 50 ng of promoter fragment and 50 ng of the fragment corresponding to the "uidA-IV2/nos term" sequence in a reaction volume of 20 µl, in the presence of 2 µl of T4 10×DNA ligase buffer (New England Biolabs) and 400 units of T4 DNA ligase (New England Biolabs). The incubation was carried out in a thermocycle by subjecting the ligation mixture to 198 cycles each consisting of a 30 sec incubation at 30° C., and a 30 sec incubation at 10° C. Previously prepared viable and competent *Escherichia coli* DH5α bacteria were transformed with half of the ligation reaction mixture. The plasmid DNA of the obtained clones, selected on LB media supplemented with tetracycline (12 mg/l), was extracted according to the alkaline lysis method and analysed by enzymatic digestion and gene amplification using the desoxynucleotides 5' ATATGAGACTCTAATTGGATACCGAGGGG 3' (SEQ ID NO:33) selected from the transfer DNA of the binary plasmid and 5' TTGATTTCACGGGTTCGG 3' (SEQ ID NO:28) selected from the expression cassette in the uidA sequence. One of the retained clones was designated pGA492MPr1092.

The plasmids pMRT1152, pMRT1171, pMRT1172 and pMRT1182 were transferred into a strain of *Agrobacterium tumefaciens* LBA4404 according to the technique described by Holsters et al. (1978). The plasmid DNA of the obtained clones, selected on LB media supplemented with rifampicin (50 mg/l) and with tetracycline (5 mg/l), was extracted according to the alkaline lysis method, modified by adding lysozyme (25 mg/ml) to the cell resuspension buffer. The plasmid DNA obtained was analysed by enzymatic digestion and gene amplification using the desoxynucleotides 5' ATATGAGACTCTAATTGGATACCGAGGGG 3' (SEQ ID NO:33) selected from the plasmid and 5' TTGATTTCACGGGTTGGG 3' (SEQ ID NO:28) selected from the expression cassette. The agrobacteria clones obtained were used to carry out plant genetic transformation.

3.5. Production of the Binary Vectors pMRT1185, pMRT1186, pMRT1187 and pMRT1188:

The expression cassettes MPr1162/uidA-IV2/nos term, MPr1164/uidA-IV2/nos term, MPr1165/uidA-IV2/nos term and MPr1167/uidA-IV2/nos term were produced from plasmids pMRT1162, pMRT1164, pMRT1165 and pMRT1167 respectively, and were cloned into the binary plasmid pMRT1118 described previously.

A 10 µg amount of each of the plasmids pMRT1162, pMRT1164, pMRT1165, and pMRT1167 were digested by PstI for 1 h at 37° C. then purified on an affinity column. The protruding 5' ends of these various opened vectors were blunted using Pfu DNA polymerase (Stratagene, La Jolla, USA) according to the supplier's recommendations. The thus treated vectors were digested again simultaneously by 20 units of EcoRI and 10 units of XmnI for 1 h at 37° C. For each of these digestions, the DNA fragment corresponding to the expression cassette was isolated on 1% agarose gel and purified on a QIAquick affinity column.

The ligation was carried out in a thermocycle sold under the trade name GENEAMP PCR System 9700 by mixing 100 ng of binary plasmid pMRT1118 prepared as described above and 50 ng of expression cassette in a reaction volume of 12 µl in the presence of 1.2 µl T4 10×ONA ligase buffer (Epicentre Technologies), 1.2 µl of 25 mM ATP solution and 3 units of 10×DNA ligase (Epicentre Technologies). The ligation reaction consisted of a series of 200 identical cycles each consisting of a 30 sec step at 10° C. and a 30 sec step at 30° C. Previously prepared, viable and competent *Escherichia coli* DH5α bacteria were transformed with half of the ligation reaction mixture. The plasmid DNA from the clones obtained, selected on LB media supplemented with kanamycin (50 mg/l), was extracted according to the alkaline lysis method and analysed by enyzmatic digestion with the enzymes BamHI and EcoRI. The resulting clones were designated pMRT1185, pMRT1186, pMRT1187, and pMRT1188, and contain respectively the promoters MPr1162, MPr1164, MPr1165 and MPr1167.

3.6. Production of Positive Control Binary Vector pMRT1182.

The binary vector pMRT1182 was obtained by insertion of the PrD35S CaMV promoter fragment and the uidA-IV2/term-nos sequence into the binary plasmid pMRT1118 prepared as described above.

The PrD35S CaMV promoter was isolated by digesting 10 μg of the plasmid pJIT163Δ successively with KpnI and HindIII for 1 h at 37° C. The 743 bp fragment corresponding to pD35S CaMV was isolated on 0.8% agarose gel, then purified on a QIAquick affinity column.

The "uidA-IV2/nos term" sequence was obtained by digesting 4 μg of plasmid pMRT1092 with 40 units of HindIII and EcoRI for 1 h. The 2.2 kb fragment corresponding to the "uidA-IV2/nos term" sequence was isolated on 0.8% agaros gel, then purified on a QIAquick affinity column.

The ligation was carried out in the presence of 100 ng of binary plasmid, 50 ng of the PD35S CaMV fragment and 50 ng of the fragment corresponding to the uidA-IV2/term-nos sequence in a reaction volume of 20 μl, in the presence of T4 (1×) DNA ligase buffer and 400 units of T4 DNA ligase (New England Biolabs). The incubation was carried Out by PCR cycles in a thermocyle sold under the trade name GENEAMP PCR System 9700, as described previously. Previously prepared, viable and competent *Escherichia coli* DH5α bacteria were transformed with half of the ligation reaction mixture. The plasmid DNA of the obtained clones, selected on LB media supplemented with kanamycin (50 mg/l), was extracted according to the alkaline lysis method and analysed by enzymatic digestion. The resulting plasmid was designated pMRT1182.

3.7. Production of Binary Vectors pMRT1245, pMRT1246, pMRT1247, pMRT1248, pMRT1249, pMRT1250, pMRT1251, pMRT1252, and pMRT1253:

The expression cassettes MPr11116/uidA-IV2/nos term, MPr1154/uidA-IV2/nos term, MPr1162/uidA-IV2/nos term, MPr1163/uidA-IV2/nos term, MPr1164/uidA-IV2/nos term, MPr1165/uidA-IV2/nos term, MPr1167/uidA-IV2/nos term, MPr1168/uidA-IV2/nos term and MPr1169/uidA-IV2/nos term were produced from plasmids pMRT1116, pMRT1154, pMRT1162, pMRT1163, pMRT1164, pMRT1165, pMRT1167, pMRT1168 and pMRT1169 respectively, and were cloned into the HpaI site of the binary vector pMRT1195. A 10 μg amount of each of the plasmids pMRT1116, pMRT1154, pMRT1162, pMRT1163, pMRT1164, pMRT1165, pMRT1167, pMRT1168, pMRT1169 was digested simultaneously by 20 units of PstI, 20 units of EcoRI and 10 units of XmnI for 1 h at 37° C. For each of these digestions, the corresponding DNA fragment to the expression cassette was isolated on 1% agarose gel and purified on a Qiaquick affinity column. The 5' protruding ends of these different fragments were blunted using Pfu DNA polymerase (Stratagene, La Jolla, USA)according to the supplier's recommendations.

Ligation was carried out in a thermocycle sold under the trade name GENEAMP PCR System 9700 by mixing 100 ng of binary vector pMRT1195 prepared as described above and 50 ng of expression cassette in a reaction volume of 12 μl in the presence of 1.2 μl of T4 10×DNA ligase buffer (Epicentre Technologies), 1.2 μl of 25 mM ATP solution and 3 units of 10×DNA ligase (Epicentre Technologies). The ligation reaction consisted in a series of 200 identical cycles each consisting of a 30 sec step at 10° C. and a 30 sec step at 30° C. Previously prepared, viable and competent *Escherichia coli* DH5α bacteria was transformed with half of the ligation reaction mixture. The plasmid DNA of the obtained clones, selected on LB media supplemented with kanamycin (50 mg/l), was extracted according to the alkaline lysis method and analysed by enzymatic digestion by the enzymes BamHI and EcoRI. The resulting clones were designated pMRT1245, pMRT1246, pMRT1247, pMRT1248, pMRT1249, pMRT1250, pMRT1251, pMRT1252 and pMRT1253, and contain respectively the promoters MPr1116, MPr1154, MPr1162, MPr1163, MPr1164, MPr1165, MPr1167, MPr1168 and MPr1169.

3.8. Production of the Positive Control Binary Vector pMRT1254.

The binary vector pMRT1254 is used as a positive control during evaluation of the expression in plants.

The expression cassette MPr1092/uidA-IV2/nos term was cloned into the HpaI site of the binary vector pMRT1195 prepared as described above. It was obtained by digesting 10 μg of plasmid pMRT1182 with 40 units KpnI for 1 h at 37° C., purification of the digestion product on an affinity column and then digestion with 40 units of EcoRI. The 2.8 kb DNA fragment corresponding to the expression cassette was isolated on 1% agarose gel and purified on a Qiaquick affinity column. The 5' protruding ends sortantes of this fragment were blunted with Pfu DNA polymerase (Stratagene, La Jolla, USA) according to the supplier's recommendations.

Ligation was carried out in a thermocycle sold under the trade name GENEAMP PCR System 9700 by mixing 100 ng of the binary vector pMRT1195 prepared as described previously with 50 ng expression cassette in a reaction volume of 12 μl in the presence of 1.2 μl T4 10×DNA ligase buffer (Epicentre Technologies), 1.2 μl of 25 mM ATP solution and 3 units of 10×DNA ligase (Epicentre Technologies). The ligation reaction consisted of a series of 200 identical cycles each consisting of a 30 sec step at 10° C. and a 30 sec step at 30° C. Previously prepared, viable and competent *Escherichia coli* DH5α bacteria were transformed with half of the ligation reaction mixture. The plasmid DNA of the obtained clones, selected on LB media supplemented with kanamycin (50 mg/l), was extracted according to the alkaline lysis method and analysed by enzymatic digestion with the enzymes BamHI and EcoRI. The resulting clone was designated pMRT1254.

3.9. Production of the Negative Control Binary Vector pMRT1255.

The binary vector pMRT1255 is used as a negative control during evalutation of the expression in plants.

The expression cassette deprived of a promoter and corresponding to the "uidA-IV2/nos term" sequence was cloned into the HpaI site of the binary vector pMRT1195, in order to use this plasmid as the negative control.

This sequence was obtained by digesting 10 μg of the plasmid pMRT1163 with 40 units of BamHI for 1 h at 37° C., purifying the digestion product on an affinity column and then digesting with 40 units of EcoRI at 37° C. for 1 h. The 2.2 kb DNA fragment corresponding to the promoter-less expression cassette was isolated on 1% agaros gel and purified on a Qiaquick affinity column. The 5' protruding ends of this fragment were blunted using Pfu DNA polymerase (Stratagene, La Jolla, USA) according to the supplier's recommendations.

Ligation was carried out in a thermocycle sold under the trade name GENEAMP PCR System 9700 by mixing 100 ng of binary vector pMRT1195 prepared as described above and 50 ng of expression cassette in a reaction volume of 12 µl in the presence of 1.2 µl of T4 10×DNA ligase buffer (Epicentre Technologies), 1.2 µl of 25 mM ATP solution and 3 units of 10×DNA ligase (Epicentre Technologies). The ligation reaction consisted of a series of 200 identical cycles each consisting of a 30 sec step at 10° C. and a 30 sec step at 30° C.

Previously prepared, viable and competent *Escherichia coli* DH5α bacteria were transformed with half of the ligation reaction mixture. The plasmid DNA of the obtained clones, selected on LB media supplemented with kanamycin (50 mg/l), was extracted according to the alkaline lysis method and analysed by enzymatic digestion with the enzymes BamHI and EcoRI. The resulting clone was designated pMRT1255.

4. Measurement and Comparison of the Levels of Expression of the Different Promoters According to the Invention Through Transient Expression Experiments.

4.1. Culture and Plant Material Production.

4.1.1 In Vitro Culture of Tobacco, Leaf Preparation.

The transient expression experiments were carried out on tobacco leaves (*Nicotiana tabacum* L.) of the cultivar PBD6 aged 6 weeks. Mature tobacco cv. PBD6 seeds were sterilised for 10 min in a saturated calcium hypochlorite solution (70 g/l), then rinsed thrice for 5 min in sterile deionized water. The sterile seeds were placed on MS20 media (Murashige et Skoog, 1962) and incubated for 6 weeks in a culture chamber (constant temperature of 24° C., photoperiod 16 h light/8 h darkness, luminous intensity of 200 µmol photons.m$^{-2}$.sec$^{-1}$).

In order to avoid the foliar mesophyll cells splitting during transformation, the 2 main leaves of the tobacco plants PBD6 aged 6 weeks were excised from the plant 24 h before transformation with a gene gun, and placed, adlignous face up, on gentle plasmolysis BY3 media (Salts MS 4,4 g/l, myoinositol 100 mg/l, thiamine 1 mg/l, KH$_2$PO$_4$ 200 mg/l, Saccharose 30 g/l, Sorbitol 45,5 g/l, 2,4 D 1 mg/l, pH 5,8).

4.1.2. Production and Preparation of Corn Seed.

Transient expression experiments were carried out on the endosperm of L2 corn seeds (cultivar SN 87 165), taken from corn plants cultured in a phytotron at 24° C., at 60% relative humidity and with a ephotoperiod of 16 h light/8 h darkness.

Twelve days after pollinisation (12 DAP), the corn seed was taken and sterilised in a 20% solution of bleach sold under the tradename DOMESTOS®, with agitation for 5 min. Following the elimination of the DOMESTOS® by successive rinsing with deionized sterilised water, the pericarp and the aleurone cell layer were carefully removed under sterile conditions. Tangential cuts of the now exposed endosperm were made and placed on filter paper soaked in the minimal Murashige et Skoog media (MS 5524, Sigma).

4.1.3. Production of Corn Leaves.

Transient expression experiments were carried out on leaves of L2 corn (cultivar SN 87 165), taken from the plant after two weeks culture in a phytotron at 24° C., at 60% relative humidity and with a photoperiod of 16 h light/8 h darkness.

Twelve days after germination, the youngest leaves were taken and sterilised in a 20% solution of bleach sold under the tradename DOMESTOS®, with agitation for 5 min. The DOMESTOS® was eliminated by successive rinsing with deionized sterilised water, then the leaves were placed for 24 h onto the weak plasmolysis media N6P6 0.4M (salts MS 3.98 g/l, vitamines N6 100 mg/l, L-proline 700 mg/l, casein hydrosylate 100 mg/l, saccharose 20 g/l, sorbitol 36,4 g/l, mannitol 36,4 g/l, 2,4 D 1 mg/l, pH 5.8, phytagel 3 g/l), adlignous face up, in order to avoid splitting of the foliar cells during transformation.

4.2. Gold Particle Coating with the Chimeric Construction DNA.

Biolistic transformation required prior deposition of DNA onto spherical gold beads of 0.6 µm in diameter that had been sterilised for 10 min in absolute ethanol (99.98%, with less than 0.02% water), washed four times in sterile deionized water, and finally stored for a maximum of 4 weeks at −20° C. in a solution of 50% glycerol.

The concentration of all of the control and test plasmids used during for the transformation experiments, was adjusted to 1 µg/µl. In each of the transformation experiments, an internal reference control (pCaMV35Sluc) was cotransformed in order to normalise the variations of GUS activity between the different experiments (Leckie et al., 1994).

The coating of DNA onto the gold beads prepared as above was carried out in a sterile chamber under laminar flux. An aliquot fraction of 1.8 mg of sterile bead suspension in 30 µl of glycerol 50%, was mixed vigorously in a vortex for 1 min, then for 10 sec with 20 µl of DNA suspension containing 4 µg of one of the plasmids to be tested and 2 µg of the reference plasmid pCaMV35Sluc. Then, 20 µl of 2.5M CaCl2 were added an mixed vigorously for 10 sec. Next, 20 µl of 0.1M spermidine was added to the mixture and the whole mixture was agitated in a vortex for a further 30 sec. The DNA coating of the beads was continued by incubating the mixture in ice for 15 min, then the coated beads were centrifuged at low velocity for 5 sec and washed twice in absolute ethanol.

After washing, the coated beads were resuspended in 32 µl absolute ethanol, subjected to ultrasound treatment three times for a duration of 2 sec each time, vigorously mixed in a vortex for 15 sec, then immediately divided into 4 identical aliquot parts on sterile "macrocarrier" disks of the Biolistic PDS-1000/He system prepared according to the supplier's recommendations (BioRad, Hercule, USA). The entire assembly of "macrocarrier support/macrocarrier bearing the bead deposit", was left to dry for 5 min.

4.3 Bombardment of Tobacco Foliar Tissues and Transient Expression.

The bombardment of tobacco leaves was carried out using a gene gun system sold under the tradename BIOLISTIC PDS-1000/HE by following the general recommendations of the supplier (BioRad, Hercule, USA) relating to the manipulations and assembly of the various components of the apparatus. Each leaf was bombarded twice successively under the following shooting conditions:

helium pressure selected for the acceleration of the coated gold beads was 6200 kPa (900 psi).

the plant sample was placed at 9 cm from the bead acceleration zone.

the shooting was carried out in a vacuum of 27 mm of mercury. After bombardment the leaves were left in BY3 media and incubated for 48 h in the dark in a culture chamber at 24° C. This incubation enabled transient expression of the transgenes introduced into the cells to occur.

4.3.1 Evaluation of the Activity of the Different Promoters by Histochemical Staining.

The revelation of the expression of β-glucuronidase was carried out by histochemical staining as described by Jefferson et al. (1987). After 48 h in the culture chamber, each leaf was cut in two along the longitudinal axis of the central rib. Half of the leaf was incubated in staining buffer for β-glucuronidase (5-bromo, 4-chloro, 3-indolyl glucuronide (X-Gluc) 500 mg/l, Triton x100 0.05% in 0.1 M phosphate buffer, pH 7.0) for 48 h at 37° C., whereas the other half was frozen in liquid nitrogen, then stored at −80° C.

After staining, the leaves were bleached by dipping them in two 95% ethanol baths for respectively 3 and 12 h, then rinsed in distilled water and dried flat between two sheets of cellophane. The results of these histochemical stainings are presented in FIG. V. The promoter activity of the various constructions was evaluated by the number of blue spots revealed on each leaf half after two shootings amounting to a total of 2 μg of DNA bearing the GUS reporter gene.

Two categories of promoters were identified. The leaves bombarded with the promoters MPr1116 and MPr1146 showed on average a number of blue spots significantly greater than 150 (FIG. VIII) compared to the number of blue spots obtained by bombarding the leaves in the same conditions and with the same amount of reference control plasmid pMRT1092. The leaves bombarded with the promoters MPr1117 and MPr1147 show an average number of blue spots comprised between 50 et 150 (cf. FIG. VIII).

To sum up, the chimeric promoters MPr1116 and MPr1146 enable or promote expression of β-glucuronidase to a level greater than or equal to that obtained using the strong constitutive reference promoter D35S prom.

4.3.2. Quantification of the Expression of β-glucuronidase with the Various Promoters, by Luminometric Enzymatic Activity Determination.

The frozen leaf halves were ground in a mortar, then the powder was left to thaw in extraction buffer (Tris Phosphate 25 mM pH 7.8, Dithiothreitol 2 mM, 1,2-diaminocyclohexane, N,N,N',N'-tetracetic acid 2 mM, glycerol 10%, Triton X100 1%) in a ratio of 1 ml of buffer to 200 mg of tissue. The mixture was homogenised then incubated for 15 min in ice before being clarified by centrifugation for 5 min at 16060 g.

GUS activity was measured on 20 μl of clarified crude leaf extract using a "GUS-Light chemiluminescent reporter gene assay" detection kit (Tropix Inc., Bedford, USA) according to the supplier's recommendations. The measurement of light emission was carried out X using a Lumat LB 9507 luminometer (EGG-Berthold, Bad Wildbad, Germany).

The luciferase activity was measured on 20 μl crude leaf extract using a "Luciferase assay system" detection kit (Promega Corp., Madison, USA) according to the supplier's recommendations. The measurement of light emission was carried out using a Lumat LB 9507 luminometer.

The results are presented in FIG. VI. For each experiment (one bombarded leaf=one crude extract), the ratio between β-glucuronidase and luciferase activities measured by the luminometer, was calculated. The average of the different experiments for a given construction and the standard mean error were determined. The results obtained show that:

The promoters MPr1116 and MPr1146 (FIG. IV) seem to significantly increase expression over that of the double 35S CaMV reference promoter (MPr1092, FIG. II). The promoter MPr1146 differs from promoter MPr1116 by the insertion of a duplication of the "as-2" box preceding the "as-1" box of the 35S CaMV promoter located between the "as-1 like" box of the CoYMV promoter and the green tissue specific element of the CsVMV promoter. This insertion of elements from the 35S CaMV promoter in MPr1146 seems to slightly increase the average degree of expression in relation to promoter MPr1116 (4.5%). These elements seem to be implicated in a positive synergy in such a combination.

The promoters MPr1116 and MPr1117 (FIG. IV) only differ with respect to the addition of an "as-1 like" box from the CoYMV promoter in MPr1117. The average expression conferred by the promoter MPr1117 is significantly lower than that obtained with MPr1116 (22%). This result suggests that the "as-1 like" element from CoYMV located in the 5' region of the chimeric promoter plays a repressor role in the promoter activity.

The promoter MPr1147 (FIG. IV) differs from promoter MPr1117 by the insertion of the "as-1" and "as-2" boxes between the "as-1 like" element from the CoYMV promoter and the green tissue specific element from the CsVMV promoter. The addition of these boxes and interaction with the other elements seems to lead to a significant reduction in the average rate of expression with respect to MPr1117 (43%). The association of these elements seems to favour a negative synergy. This can be used in constructs where the level of expression required in the transformed cell is relatively low, for example when providing antibiotic or herbicide resistance for selection or marking purposes. Nevertheless, the weakest expression conferred by the promoter MPr1147 only differs by 51% to that obtained by the promoter MPr1092. This negative effect could be explained in the case of the chimeric promoter, by a competition with trans-activating elements or else by a steric hindrance effect of these factors on the promoter, thus diminishing its activity.

To conclude, the chimeric promoters MPr1116 and MPr1146 seem to cause an average expression of the GUS reporter gene in tobacco leaves that is noticeably better than that obtained by MPr1092. This latter promoter is commonly reported in the literature as being the strongest chimeric promoter (of the order of 10 times greater than the strong constitutive promoter CaMV p35S (Kay et al., 1987), and routinely used for transgenesis. MPr1116 and MPr1146 can thus be classed among the strongest chimeric promoters known to date.

The weaker expressing promoters can be of interest as mentioned above as promoters used for conferring antibiotic resistance for the purposes of selection, for example in the same way as promoters of the "nos" type.

FIG. IX illustrates complementary results. For each experiment, the ratio between β-glucuronidase activity and luciferase activity measured with the luminometer was calculated. The mean average of the different experiments for a given construction and standard mean error were determined. The results obtained show that:

the promoters MPr1163 and MPr1165 (cf. FIG. VII), much as the promoters MPr1116 and MPr1146 (cf. FIG. VII) are responsible for an average expression of the reporter gene slightly greater, by 8%, 5%, 6.5% and 11.5% respectively, than that obtained by the reference promoter MPr1092. The promoters MPr1163 and MPr1165 differ from the promoter MPr1116 by the insertion of respectively 2 and 4 series of as-2/as-2/as-1 boxes immediately downstream of the green tissue specific region from the CsVMV promoter. This insertion of multiple boxes from the CaMV 35S promoter into MPr1116 does not enable an increase in the average degree of expression with respect to that of promoter MPr1116.

the comparison of the average activity of the promoters MPr1146 and MPr1162 reveal that cloning into MPr1116 of the series of activating elements "as-2/as-2/as-1" from the CaMV promoter into the 5' region of the green tissue specific region of the CsVMV promoter, which is the case for MPr1146, is more favorable than cloning these same elements into the 3' region of this sequence, which is the case for MPr1162. This data indicates that the position of the activating elements with respect to each other is significantly related to the capacity of the promoter to transcribe efficiently. There is thus a synergy between the activating elements.

the comparison of the average activity of the promoters MPr1162, MPr1163 and MPr1165 reveals that multiplication of the as-2/as-2/as-1 boxes immediately downstream of the green tissue specific region of the CsVMV promoter does not provide a significant proportional increase in the activity of these promoters in transient expression. This data tends to show that there is no positive synergy between the whole of these activating element boxes assembled in such combinations. Without wishing to be limited by theory, this could be explained by competition with trans-activating elements or else by steric hindrance problems of these trans-activating elements on the promoter.

the reported negative effect of the "as-1like" box from CoYMV that had been mentioned above during comparison of the activity of the promoters MPr1116, which has only one such box, and MPr1117, which has two such boxes, is confirmed. The deletion of these "as-1 like" boxes in promoter MPr1154 with respect to promoter MPr1147 enables a significant 65% increase in the activity of the promoter.

the promoters MPr1162 and MPr1164 (FIG. VII) only differ from the orientation of the series of as-2/as-2/as-1 boxes from CaMV downstream of the CsVMV sequence. No significant difference between these two promoters was observed. The orientation of these boxes does not therefore appear, at least in the current configuration, to have any repercussions on the activity of the chimeric promoter.

To conclude, the chimeric promoters MPr1163 and MPr1165 seem to provoke an average expression of the GUS reported gene in tobacco leaves at least as great as that obtained with the promoter MPr1092. The chimeric promoters MPr1163 and MPr1165, much as the promoters MPr1116 and MPr1146 can thus be classed among the strongest chimeric promoters described to date and can therefore be used routinely in transgenesis programs for dicotyledonous plants, as a substitute to the CaMV D35S (double 35S or enhanced) promoter.

4.4. Corn Bombardment and Transient Expression.

The bombardment of various corn tissues, and among others young leaves and albumen, was carried out with a gene gun system sold under the tradename BIOLISTIC PDS-1000/HE using the general recommendations of the supplier (BioRad, Hercule, USA) in relation to the manipulations and assembly of the different components of the apparatus. Each endosperm was bombarded twice in succession with tungsten particles of 0.6 $\mu$m diameter, using the following shooting conditions:

the helium pressure to accelerate the particles was 6200 kPa (900 psi), the plant sample was placed at 6 cm from the particle acceleration zone, the shooting was carried out in a vacuum of 27 mm of mercury. Following bombardment, the endosperm were left in position and incubated for 24 h in the dark in a culture chamber at 26° C., to enable transient expression of the transgenes introduced into the cells.

4.5. Evaluation of the Activity of Different Promoters in Corn Endosperm by Histochemical Staining.

Revelation of the expression of β-glucuronidase was carried out by histochemical staining as described by Jeffersson et al. (1987). After 24 h in a culture chamber, each portion of endosperm was incubated for 48 h at 37° C. in the presence of the substrate 5-bromo,4-chloro,3-indolyl glucuronide, X-Gluc at 500 mg/l in a 0.1 M phosphate buffer at pH 7.0 to which Triton x100 0.05% had been added.

After staining, the portions of endosperm were rinsed in water then stored in a 96% ethanol bath.

The promoter activity of the different constructions were evaluated by the number of blue spots revealed on each portion of endosperm after two bombardments totaling 2 $\mu$g of DNA bearing the GUS reporter gene.

Analysis of the results of the histochemical stainings revealed that two categories of promoters could be identified. The endosperm bombarded with the promoters MPr1092, MPr1116, MPr1146 and MPr1147 showed on average relatively few blue spots of small diameter, ranging from 0 to 15 in number. The endosperm bombarded with the promoters MPr1154, MPr1162, MPr1163, MPr1164, MPr1167 and MPr1169, and the reference control promoter MPr1218 showed a number of blue spots comprised between 10 and 30, the diameter of which was greater than those obtained with the above previously described promoters.

4.6. Evaluation of β-glucuronidase Expression in Corn Endosperm Using Luminometric Enzyme Assay Measurement.

Frozen portions of endosperm were ground in a tube in extraction buffer (Tris Phosphate 25 mM pH 7.8, Dithiothreitol 2 mM, 1,2-diaminocyclohexane N,N,N',N'-tetracetic acid 2 mM, glycerol 10%, Triton X100 1%) using 1 ml of buffer for 200 mg of tissue. The mixture was homogenized then incubated for 15 min in ice before being clarified by centrifugation for 5 min at 16060 g. GUS activity was measured on 20 $\mu$l of clarified crude extract using a "GUS-Light chemiluminescent reporter gene assay" detection kit (Tropix Inc., Bedford, USA) according to the supplier's recommendations. The measurement of light emission was carried out using a Lumat LB 9507 luminometer (EGG-Berthold, Bad Wildbad, Germany).

Luciferase activity was measured on 20 $\mu$l crude extract using a "Luciferase assay system" detection kit (Promega Corp., Madison, USA) according to the supplier's recommendations. The measurement of emitted light was carried out using a Lumat LB 9507 luminometer.

The results are presented in FIG. VIII. For each crude extract, the relationship between β-glucuronidase activity and luciferase activity as measured by the luminometer, was calculated. The average of the different experiments for a given construction and standard mean error were determined. The results obtained show that the original chimeric viral promoter MPr1116 confers an activity 3.8 times greater than that obtained with the reference promoter MPr1218. This shows that the chimeric promoter, which contains "endosperm like" boxes possesses the necessary signals for expression of the GUS reporter gene in corn seed. The chimeric promoters MPr1162, MPr1163, MPr1164 and Mpr1165, which derive from promoter Mpr1116, have an activity comprised between 4.7 and 6 times that obtained with MPr1218 and between 1.2 and 1.6 times that obtained with MPr1116. Taking into account the fact that all of the chimeric promoters derived from MPr1116 possess the same basic sequence comprising the same regulatory elements or boxes apart from the activating elements from the CaMV promoter, the differences in activity observed seem to be due to the activating elements taken from CaMV.

The promoters containing a duplication of the "as-1 like" box from CoYMV, which is the case for promoters MPr1167, MPr1168 and MPr1169, all show on average an activity that is significantly less than the promoters that only contain a single "as-1 like" box, as is the case for promoters MPr1162, MPr1163, MPr1164 and MPr1165. These results seem to confirm the repressor effect of this element from CoYMV, already observed for transient expression in tobacco. However, the comparison of average activities conferred by the promoters MPr1116 and MPr1154 shows that the absence of the "as-1 like" box and its replacement by an activiating sequence "as-2/as-1" from CaMV in MPr1154, does not lead to an increase in activity with respect to MPr1116. It would therefore appear that it is the position of the boxes immediately in the 5' region of the 104 bp sequence of CsVMV which is unfavorable for the activity rather than the boxes themselves.

Without wishing to be bound by theory, it is likely that the attachment of trans-activators in this position provokes a conformational change in the whole of the "promoter sequence/protein" assembly, and that this is unfavorable to the attachment of other activating elements and/or the transcriptional machinery.

The analysis of the results reveals that the number of repetitions of the combination of "as-2/as-2/as-1" boxes probably conditions the activity of the chimeric promoter. For example, an increase in the average activity between MPr1162, which possesses a single series of elements, MPr1163, which has two such series, and MPr1165, which has 4 such series, was observed, even if the differences do not appear very significant. In the same way, the activity increases between MPr1169, MPr1168 and MPr1167 which respectively have 1, 2 and 3 series of boxes.

Finally, the orientation of these activating boxes or elements does not seem to have any repercussions on the activity since no significant difference was observed between the promoters MPr1162 and MPr1164.

To conclude, the chimeric promoters created according to the present invention are functional and operational in monocotyledonous plants and show in particular strong activity in corn albumen. The promoters MPr1163 and MPr1165 are the promoters that show the greatest activity of the GUS gene in transient expression in corn endosperm 12 days after pollenisation. This activity is of a high level since it is about 6 times higher than that obtained with the strong promoter responsible for the active expression of gammazein, the major storage protein in corn albumen. These promoters can therefore be routinely used in transgenesis programs for monocotyledonous plants as an efficient alternative to other heterologous promoteurs.

5. Expression of the Different Promoters in Tobacco After Stable Transformation.

5.1. Stable Transformation of Tobacco.

Tobacco transformation (*Nicotiana tabacum* L., cultivar PBD6) was carried out by infecting foliar disks isolated from tobacco plants aged 6 weeks with recombinant Agrobacteria according to the method described by Horsch et al. (1985).

During transformation, the Petri dishes were incubated in a culture chamber under the following conditions: temperature of 24° C., photoperiod of 16 h night/8 h jour, luminous intensity of 200 $\mu$mol photons.m$^{-2}$.sec$^{-1}$, and apart from the initial coculture step, the whole of the callogenesis, regeneration and rooting steps were carried out on different selective media supplemented with Augmentin® (400 mg/l) and kanamycin (200 or 100 mg/ml);

The various steps and media used are the following:—a coculture step lasting three days, during which the Agrobacteria infect the plant cells, on a solid MS30 coculture media (media with MS base (Murashige et Skoog, 1962) supplemented with vitamins (Gamborg et al., 1968) 4.4 g/l (Sigma, M0404), Saccharose 30 g/l, agar 8 g/l (Merck), pH 5.7) supplemented with Benzyl Amino Purine at 1 mg/l and Indol-3 Acetic Acid at 0.1 mg/l.

two bud formation steps lasting two weeks each in a culture chamber on a solid MS20 regeneration media (Salts and vitamins, MS 4.4 g/l (Sigma, M0404), Saccharose 20 g/l, agar 8 g/l (Merck), pH 5.7), supplemented with Benzyl Amino Purine at 1 mg/l, Indol-3 Acetic Acid at 0.1 mg/l, Augmentin® at 400 mg/l et kanamycine at 200 mg/l.

a development and rooting step lasting 3 weeks in a culture chamber on a solid MS20 development media supplemented with Augmentin® at 400 mg/l and kanamycine at 100 mg/l.

a repotting step into glass pots in a culture chamber on a solid MS20 development media supplemented with Augmentin® at 400 mg/l and kanamycine at 100 mg/l.

5.2. Measurement and Comparison of β-glucuronidase Activity in Regenerated Tobacco Plants.

β-glucuronidase activity was measured on samples of first generation transgenic plants, taken at 2 weeks after their acclimatisation in a greenhouse. For each plant, three leaf samples were taken, one from an "aged" leaf (located the basal foliar level), one from a mature leaf (located at a median foliar level), and one from a young leaf (located at the plant apex).

Each sample was ground in liquid nitrogen in a mortar and then the powder was resuspended in extraction buffer (Tris Phosphate 25 mM pH 7.8, Dithiothreitol 2 mM, 1,2-diaminocyclohexane, N,N,N',N'-tetracetic acid 2 mM, glycerol 10%, Triton X100 1%) in a ration of 1 ml of buffer for 200 mg of tissue. The mixture was homogenised then incubated for 15 mm in ice before being clarified by centrifugation for 5 min at 16060 g.

GUS activity was measured on 20 $\mu$l clarified crude leaf extract using a "GUS-Light chemiluminescent reporter gene assay" detection kit (Tropix Inc., Bedford, USA) according to the supplier's recommendations. The measurement of light emission was carried out using a luminometer sold under the tradename LUMAT LB 9507 (EGG-Berthold, Bad Wildbad, Germany).

The quantity of total protein present in the crude extract was measured according to Bradford technique (1976), using a protein assay sold under the tradename BIORAD (BioRad, München, Germany).

Cited References

An G. (1986). Development of plant promoter expression vector and their use for analysis of differential activity of nopaline synthase promoter in transformed tobacco cells. Plant Physiol. 81, 86–91.

Barany F. (1991). The ligase chain reaction in a PCR world. PCR Methods Appl. 1, 5–16.

Birnboim H. C. et Doly J. (1979). A rapid alkaline extraction procedure for screening recombinant plasmid DNA. Nuc. Ac. Res. 7, 1513.

Bradford M. (1976). A rapid and sensitive method for the detection of microgram quantities of proteins utilizing the principle of protein-dye binding. Anal. Biochem. 72, 248–254.

Fromm M. E., Taylor L. P. et Walbot V. (1986). Stable transformation of maize after gene transfer by electroporation. Nature, 319, 791–793.

Gamborg O. L., Miller R. A. et Ojima K. (1968). Nutrient requirements of suspension cultures of soybean root cells. Exp. Cell Res. 50, 151–158.

Gaubier P., Raynal M., Hull G., Huestis G. M., Grellet F., Arenas C., Pages M. et Delseny M. (1993). Two different Em-like genes are expressed in Arabidopsis thaliana seeds during germination. Mol. Gen. Genet. 238, 409–418.

Guérineau et Mullineaux (1993). In Plant molecular biology labfax, Croy R. R. D. (Ed.), BioS Scientific Publishers, Blackwell Scientific Publications.

Jefferson R. A., Burgess S. M. et Hirsh D (1986). b-Glucuronidase as a gene-fusion marker. Proc. Nat. Acad. Sci. USA, 83, 8447–8451.

Jefferson R. A., Kavanagh T. A. et Bevan M. W. (1987). GUS fusions: β-glucuronidase as a sensitive and versatile gene fusion marker in higher plants. EMBO J. 6, 3901–3907.

Hanahan D. (1983). Studies on transformation of *Escherichia coli* with plasmids. J. Mol. Biol. 166, 557.

Holsters M., Dewaele D., Depicker A., Messenf E., Van Montagu M. etn Schell J. (1978). Transfection and transformation of *Agrobacterium tumefaciens*. Mol. Gen. Genet. 136, 181–187.

Horsch R. B., Fry J. E., Hoffmann N. L., Eiholtz D., Rogers S. G. et Fraley R. T. (1985). A simple and general method for transfer ring genes into plants. Science 227, 129–1231.

Kay R., Chan A., Daly M. et McPherson J. (1987). Duplication of CaMV 35S promoter sequences creates a strong enhancer for plant genes. Science 236, 1299–1302.

Lam E., Benfey P. N., Gilmartin P. M., Fang R. X. et Chua N. H. (1989). Site-specific mutations alter in vitro factor binding and change promoter expression pattern in transgenic plants. Proc. Natl. Acad. Sci. USA, 86, 7890–7894.

Lam E. et Chua N. H. (1989). ASF-2: a factor that binds to the cauliflower mosaic virus 35S promoter and a conserved GATA box in Cab promoters. Plant Cell, 1, 1147–1156.

Last D. I. et Gray J. C. (1989). Plastocyanin is encoded by a single-copy gene in the pea haploid genome. Plant Mol. Biol. 12, 655–666.

Leckie L., Devoto A. and Lorenzo G. (1994). Normalization of GUS by LUC activity from the same cell extract reduces transformation variability. Biotechniques 17, 52–56.

Murashige T. et Skoog F. (1962). A revised medium for rapid growth and bioassays with tobacco tissue cultures. Physiol. Plant. 15, 473–497.

Medberry S. L., Lockhart B. E. L. and Olszewski N. E. (1992). The Commelina Yellow Mottle Virus promoter is a strong promoter in vascular and reproductive tissues. Plant Cell, 4, 185–192.

Pwee K. H. et Gray J. C. (1993). The pea plastocyanin promoter directs cell-specific but not full light-regulated expression in transgenic tobacco plants. Plant J. 3, 437–449.

Sanger F., Nicklen S. et Coulson A. R. (1977). DNA sequencing with chain-terminating inhibitors. Proc. Natl. Acad. Sci. USA, 74, 5463–5467.

Torrent M., Alvarez I., Geli M. I., Dalcol I. et Ludevid D. (1997). Lysine-rich modified g-zein accumulate in protein bodies of transiently transformed maize endosperms. Plant Mol. Biol. 34, 139–149.

Vancanneyt G., Schmidt R., O'Connor-Sanchez A., Willmitzer L. et Rocha-Sosa M. (1990). Construction of an intron-containing marker gene: Splicing of the intron in transgenic plants and its use in monitoring early events in *Aqrobacterium*-mediated plant transformation. Mol. Gen. Genet. 220, 245–250.

Verdaguer B., of Kochko A., Beachy R. N. and Fauquet C. (1996). Isolation and expression in transgenic tobacco and rice plants of the Cassava Vein Mosaic Virus (CsVMV) promoter. Plant Mol. Biol. 31, 1129–1139.

What is claimed is:

1. A chimeric expression promoter comprising at least one nucleic acid sequence comprising a Commelina Yellow Mottle Virus plant promoter wherein a plant vascular expression promoter region of said Commelina Yellow Mottle Virus plant promoter is replaced with a nucleic acid sequence comprising a Cassava Vein Mosaic Virus plant promoter comprising a plant green tissue expression promoter region.

2. The chimeric expression promoter of claim 1, wherein said nucleic acid sequences originate from the intergenic regions of said Commelina Yellow Mottle Virus and Cassava Vein Mosaic Virus plant promoter.

3. The chimeric expression promoter of claim 1, comprising the nucleic acid sequence of SEQ ID NO: 1, but not including a plant vascular expresssion promoter region of said SEQ ID NO: 1 fused to a nucleic acid sequence comprising a plant green tissue expression promoter region of SEQ ID NO: 2.

4. The chimeric expression promoter of claim 1, wherein the nucleic acid sequence of said chimeric expression promoter consists of a sequence selected from the group consisting of the sequences with SEQ ID NOS: 3–7 and 19–25.

5. The chimeric expression promoter of claim 1, further comprising at least one endosperm like box.

6. The chimeric expression promoter of claim 1, further comprising at least one as1 like box operably linked to a plant green tissue expression GT promoter element.

7. The chimeric expression promoter of claim 1, further comprising at least one as1 box operably linked to a green tissue expression GT promoter element.

8. The chimeric expression promoter of claim 1, further comprising at least one as2 box operably linked to a plant green tissue expression GT promoter element.

9. The chimeric expression promoter of claim 1, comprising at least one as1 like, as1, and as2 box operably linked upstream or downstream to the plant green tissue expression GT promoter element.

10. The chimeric expression promoter of claim 1, comprising at least one as1 like, as1, and as2 box operably linked in 5' to 3' or 3' to 5' orientation.

11. The chimeric expression promoter of claim 1, comprising at least one as2/as2/as2 box in 5' to 3' or 3' to 5' orientation.

12. A chimeric expression promoter comprising a Commelina Yellow Mottle Virus promoter, of which a plant vascular expression promoter region is replaced with an exogenous Cassava Vein Mosaic Virus element which promotes expression in plant green tissues.

13. The chimeric expression promoter of claim 12, further comprising at least one endosperm like box.

14. The chimeric expression promoter of claim 12, further comprising at least one as1 like box operably linked to a plant green tissue expression GT promoter element.

15. The chimeric expression promoter of claim 12, further comprising at least one as1 box operably linked to a green tissue expression GT promoter element.

16. The chimeric expression promoter of claim 12, further comprising at least one as2 box operably linked to a plant green tissue expression GT promoter element.

17. The chimeric expression promoter of claim 12, comprising at least one as1 like, as1, and as2 box operably linked upstream or downstream to the plant green tissue expression GT promoter element.

18. The chimeric expression promoter of claim 12, comprising at least one as1 like, as1, and as2 box operably linked in 5' to 3' or 3' to 5' orientation.

19. The chimeric expression promoter of claim 12, comprising at least one as2/as2/as2 box in 5' to 3' or 3' to 5' orientation.

20. The chimeric expression promoter of claim 12, comprising at least one sequence selected from the group consisting of the sequences of SEQ ID NOS: 3–7 and 19–25.

21. An expression cassette comprising at least one first nucleic acid sequence comprising a Commelina Yellow Mottle Virus plant promoter wherein a plant vascular expression promoter region of said Commelina Yellow Mottle Virus plant promoter is replaced with a second nucleic acid sequence comprising a Cassava Vein Mosaic Virus plant promoter comprising a plant green tissue expression promoter region, said at least one nucleic acid sequence being operably linked to a third nucleic acid sequence or gene coding for a polypeptide to be produced, said third nucleic acid sequence or gene itself operably linked to a transcription termination nucleic acid sequence.

22. The expression cassette of claim 21, wherein the at least one nucleic acid sequence comprises the nucleic acid sequence of SEQ ID NO: 1, but not including a plant vascular expression promoter region of said SEQ ID NO: 1 fused to a nucleic acid sequence comprising a plant green tissue expression promoter region of SEQ ID NO: 2.

23. The expression cassette of claim 21, comprising a nucleic acid sequence selected from the group consisting of the sequences of SEQ ID NOS: 3–7 and 19–25, said nucleic acid sequence being operably linked to a nucleic acid sequence or a gene encoding for a polypeptide to be produced, said nucleic acid sequence or gene operably linked to a transcription termination nucleic acid sequence.

24. An isolated promoter nucleic acid sequence comprising a fusion of the sequences of SEQ ID NO: 01, but not including a plant vascular expression promoter region of said SEQ ID NO: 01, and a nucleic acid sequence comprising a plant green tissue expression promoter region of SEQ ID NO. 02.

25. The isolated promoter nucleic acid sequencer of claim 24, corresponding to any one of the sequences set forth in SEQ ID NO: 03, SEQ ID NO: 04, SEQ ID NO: 05, SEQ ID NO: 06, SEQ ID NO: 07, SEQ ID NO: 19, SEQ ID NO: 20, SEQ ID NO: 21, SEQ ID NO: 22, SEQ ID NO: 23, SEQ ID NO: 24, and SEQ ID NO: 25.

26. A vector comprising an isolated promoter nucleic acid sequence which initiates transcription of a nucleic acid sequence coding for a polypeptide, wherein said isolated promoter nucleic acid sequence comprises a chimeric expression promoter nucleic acid sequence according to claim 1, 12, or 25.

27. The vector of claim 26, wherein said vector is selected from the group consisting of the binary vectors pMRT1152, pMRT1171, pMRT1172, pMRT1185, pMRT1186, pMRT1187, pMRT1188, pMRT1182, pMRT1245, pMRT1246, pMRT1247, pMRT1248, pMRT1249, pMRT1250, pMRT1251, pMRT1252, pMRT1253 and pMRT1254.

28. A transgenic plant comprising at least one stably integrated promoter nucleic acid sequence according to claim 1, 12, or 25.

29. The transgenic plant of claim 28, wherein said plant is a dicotyledonous species selected from the group consisting of potato, tobacco, cotton, lettuce, tomato, melon, cucumber, pea, rape, beetroot, and sunflower, or from a monocotyledonous species selected from the group consisting of wheat, barley, oat, rice, and corn.

30. A propagule of the transgenic plant according to claim 29.

31. The propagule of claim 30, wherein the propagule is a seed.

32. A cell containing a promoter nucleic acid sequence according to claim 1, 12, or 25, wherein said cell is selected from the group consisting of a plant cell, human cell, animal cell, insect cell, bacterial cell, yeast cell, fungal cell, algal cell, and microalgal cell.

33. The cell of claim 32, wherein the cell is a plant cell.

34. A method for expressing a nucleic acid sequence coding for a polypeptide by a cell, wherein said method comprises:

(a) transforming said cell with a vector comprising at least one promoter nucleic acid sequence according to claim 1, 12, or 25; and (b) culturing said cell and expressing said polypeptide encoded by said sequence in said cell.

35. The method of claim 34, wherein said cell is a prokaryotic or an eukaryotic cell.

36. The method of claim 35, wherein said cell is a cell selected from the group consisting of bacterial cells, fungal cells, yeast cells, insect cells, human cells, animal cells, algal cells, microagal cells and plant cells.

37. The method of claim 34, wherein said cell is a plant cell.

38. A method for manufacturing a transgenic plant or a propagule of said transgenic plant, wherein said method comprises:

(a) transforming a plant cell with a vector comprising at least one promoter nucleic acid sequence according to claim 1, 12, or 25;

(b) selecting said plant cell comprising said promoter nucleic acid sequence; and (c) propagating said selected plant cell by culture or by regeneration of whole chimeric or transgenic plants.

* * * * *